(12) United States Patent
Schmitz

(10) Patent No.: US 9,254,585 B2
(45) Date of Patent: Feb. 9, 2016

(54) FORMING OF CONSOLIDATION REGIONS IN A WEB AND A WEB COMPRISING SUCH REGIONS

(75) Inventor: Christoph Schmitz, Euskirchen-Stotzheim (DE)

(73) Assignee: CONCEPTS FOR SUCCESS (C4S), Euskirchen-Stotzheim (DE)

( * ) Notice: Subject to any disclaimer, the term of this patent is extended or adjusted under 35 U.S.C. 154(b) by 213 days.

(21) Appl. No.: 13/824,801

(22) PCT Filed: Sep. 30, 2011

(86) PCT No.: PCT/EP2011/067203
§ 371 (c)(1),
(2), (4) Date: Apr. 1, 2013

(87) PCT Pub. No.: WO2012/042055
PCT Pub. Date: Apr. 5, 2012

(65) Prior Publication Data
US 2013/0183476 A1  Jul. 18, 2013

(30) Foreign Application Priority Data

| Oct. 1, 2010 | (GB) | 1016533.0 |
| Jun. 6, 2011 | (GB) | 1109418.2 |
| Jul. 28, 2011 | (GB) | 1113003.6 |

(51) Int. Cl.
*B32B 37/00* (2006.01)
*B29C 35/02* (2006.01)
(Continued)

(52) U.S. Cl.
CPC ............ *B29C 35/0261* (2013.01); *B29C 65/08* (2013.01); *B29C 65/085* (2013.01);
(Continued)

(58) Field of Classification Search
CPC .... B29C 65/08; B29C 65/083; B29C 65/085; B29C 66/21; B29C 66/45; B29C 66/81457; B29C 66/83411
USPC ............ 156/555, 580, 580.1, 580.2, 581, 582
See application file for complete search history.

(56) References Cited

U.S. PATENT DOCUMENTS

| 3,756,880 A | 9/1973 | Graczyk |
| 3,949,127 A | 4/1976 | Ostermeier et al. |

(Continued)

FOREIGN PATENT DOCUMENTS

| EP | 1346818 | 9/2003 |
| WO | 9914415 | 3/1999 |

(Continued)

OTHER PUBLICATIONS

International Search Report for PCT/EP2011/067203, Completed by the European Patent Office on Nov. 18, 2011, 2 Pages.

*Primary Examiner* — James Sells
(74) *Attorney, Agent, or Firm* — Brooks Kushman P.C.

(57) ABSTRACT

An apparatus and methods for thermally treating webs having thermoplastic respectively meltable compounds, thereby creating cylindrical or elliptic consolidation regions which may optionally have an aperture by employing a thermal energy source, such as ultrasonic energy, as well as to webs with elliptic consolidation regions. In a particular, the apparatus and methods create consolidation regions by using an anvil with a flexible elongated member, such as a wire, a chain or a tubular anvil with circumferential ribs.

18 Claims, 14 Drawing Sheets

(51) Int. Cl.
*B29C 65/08* (2006.01)
*B29C 65/00* (2006.01)
*D04H 1/544* (2012.01)
*D04H 1/555* (2012.01)
*D04H 1/559* (2012.01)
*B29C 65/02* (2006.01)

(52) U.S. Cl.
CPC .............. *B29C 66/21* (2013.01); *B29C 66/45* (2013.01); *B29C 66/69* (2013.01); *B29C 66/7294* (2013.01); *B29C 66/81453* (2013.01); *B29C 66/81457* (2013.01); *B29C 66/836* (2013.01); *B29C 66/83411* (2013.01); *D04H 1/544* (2013.01); *D04H 1/555* (2013.01); *D04H 1/559* (2013.01); *B29C 65/02* (2013.01); *B29C 65/086* (2013.01); *B29C 66/71* (2013.01); *B29C 66/727* (2013.01); *B29C 66/81264* (2013.01); *B29C 66/81469* (2013.01); *B29K 2995/007* (2013.01); *Y10T 428/19* (2015.01); *Y10T 428/24273* (2015.01); *Y10T 428/24314* (2015.01); *Y10T 428/24496* (2015.01); *Y10T 428/24595* (2015.01); *Y10T 428/24603* (2015.01)

(56) References Cited

U.S. PATENT DOCUMENTS

| | | | |
|---|---|---|---|
| 3,966,519 | A | 6/1976 | Mitchell et al. |
| 4,531,999 | A * | 7/1985 | Persson et al. ............. 156/580.2 |
| 5,620,779 | A | 4/1997 | Levy et al. |
| 5,964,742 | A | 10/1999 | McCormack et al. |
| 6,220,490 | B1 | 4/2001 | O'Hara |
| 6,457,626 | B1 | 10/2002 | Sheehan et al. |
| 6,517,650 | B2 | 2/2003 | Couillard et al. |
| 6,517,651 | B2 | 2/2003 | Azulay |
| 6,517,671 | B2 * | 2/2003 | Couillard et al. .......... 156/580.2 |
| 6,607,810 | B1 | 8/2003 | Boich |
| 6,713,159 | B1 | 3/2004 | Blenke et al. |
| 7,341,084 | B2 * | 3/2008 | Van Eperen ................. 156/510 |
| 7,892,375 | B2 | 2/2011 | Blanchard et al. |
| 7,914,723 | B2 | 3/2011 | Kim et al. |
| 2007/0117481 | A1 * | 5/2007 | Day et al. ........................ 442/50 |
| 2010/0305543 | A1 | 12/2010 | Klaska |

FOREIGN PATENT DOCUMENTS

| | | |
|---|---|---|
| WO | 0027626 | 5/2000 |
| WO | 2008065365 | 5/2008 |
| WO | 2008129138 | 10/2008 |
| WO | 2009021473 | 2/2009 |

* cited by examiner

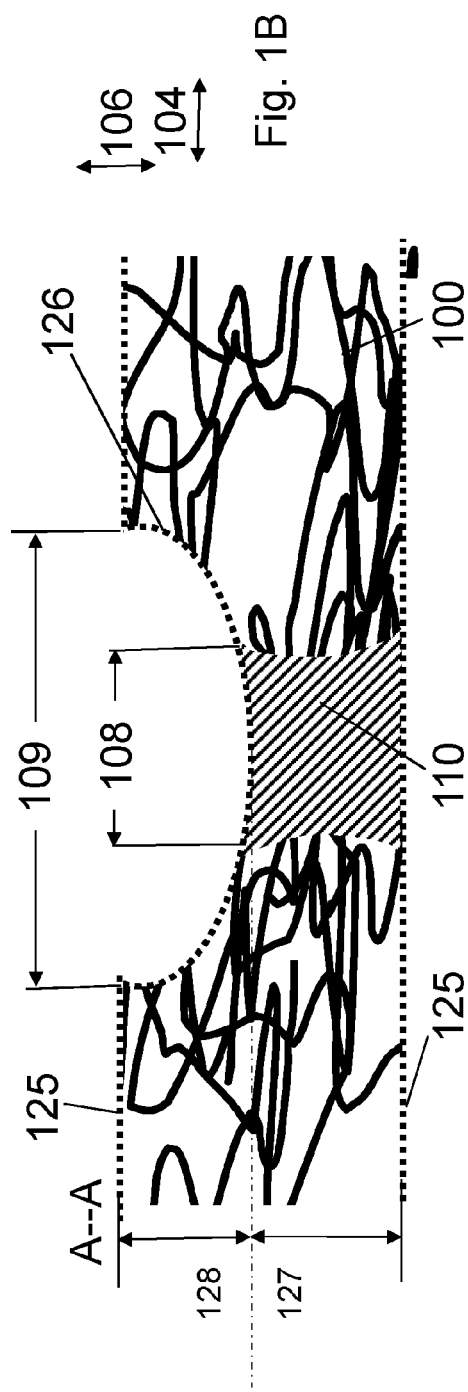
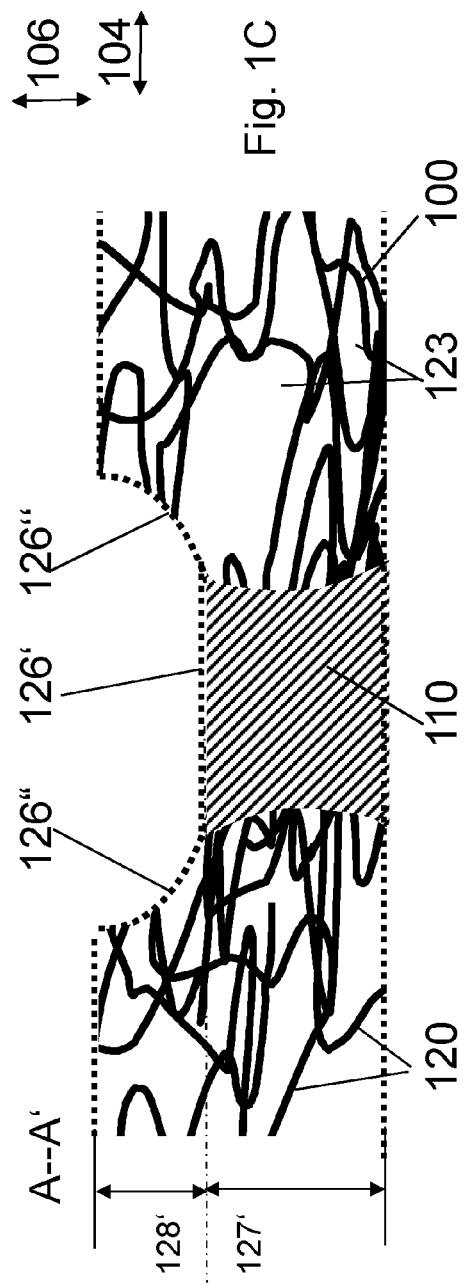
Fig. 1B
Fig. 1C

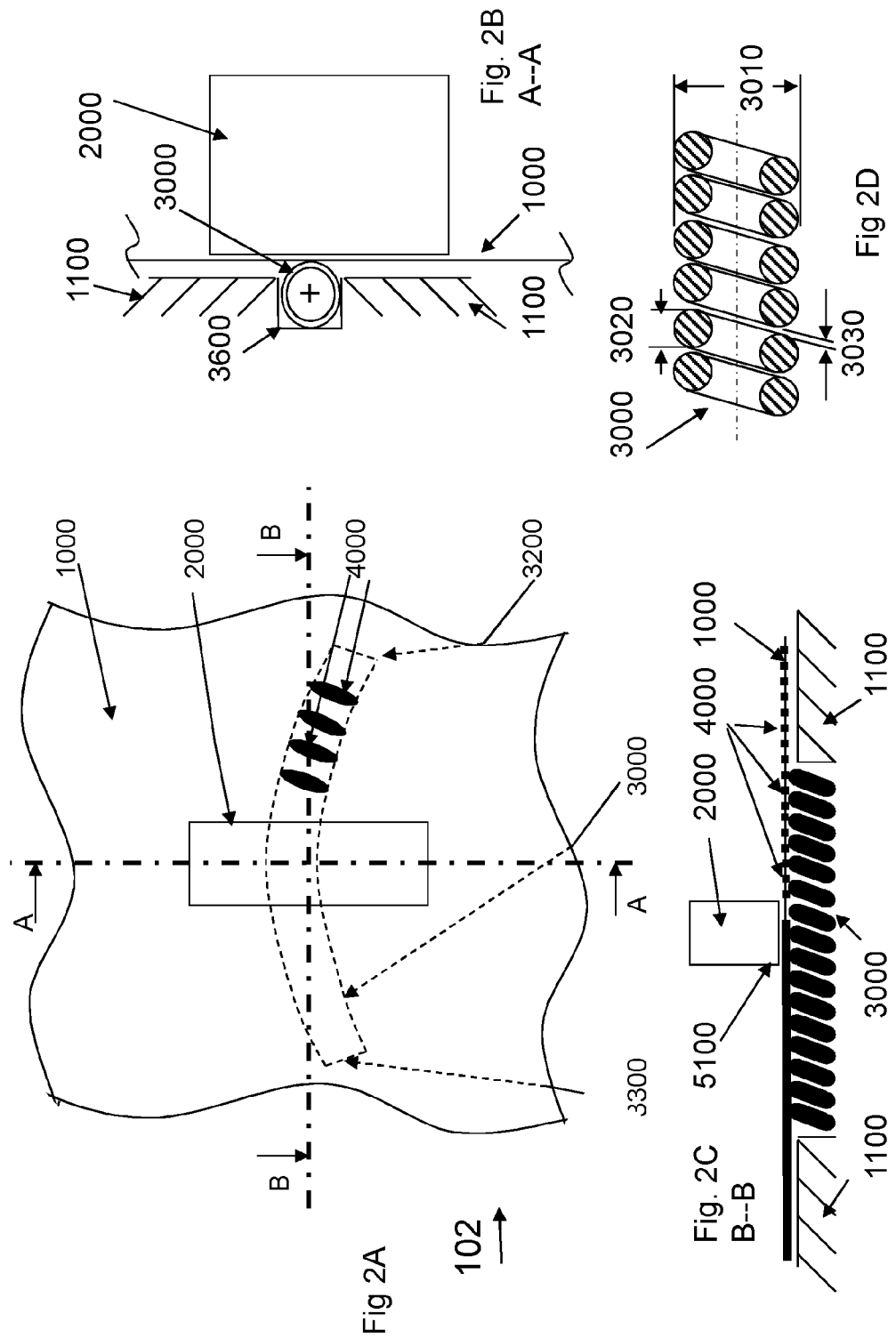

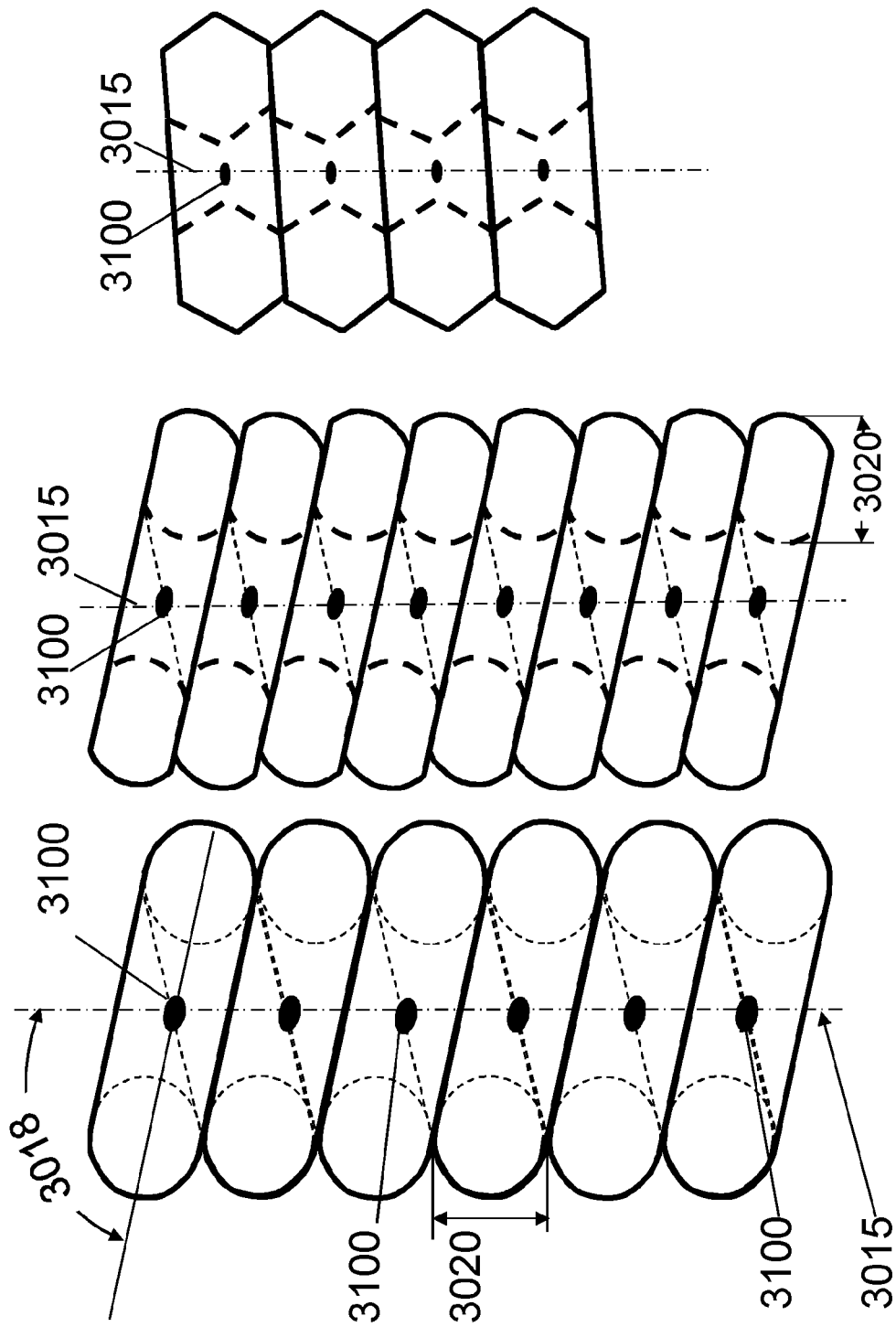

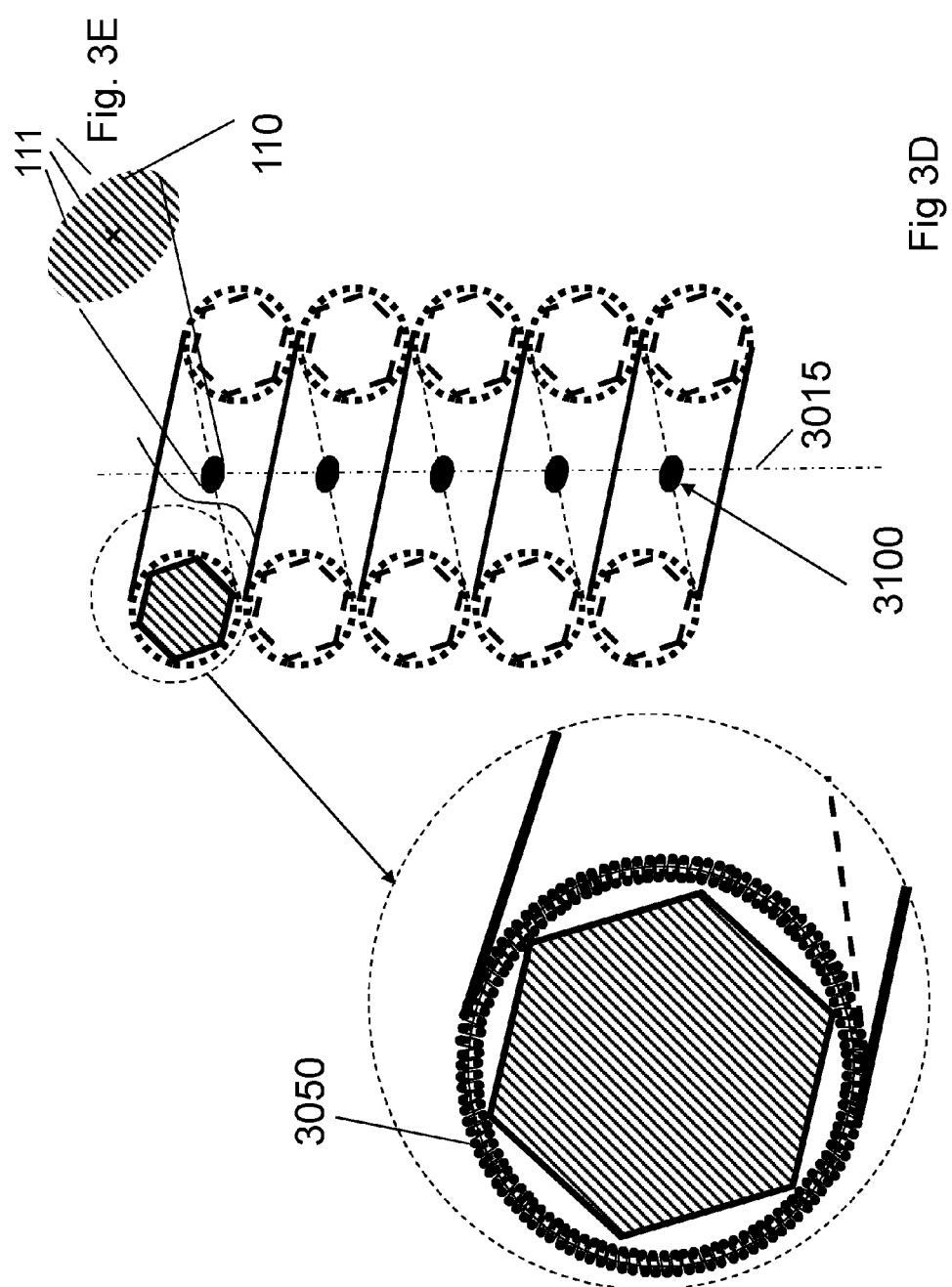

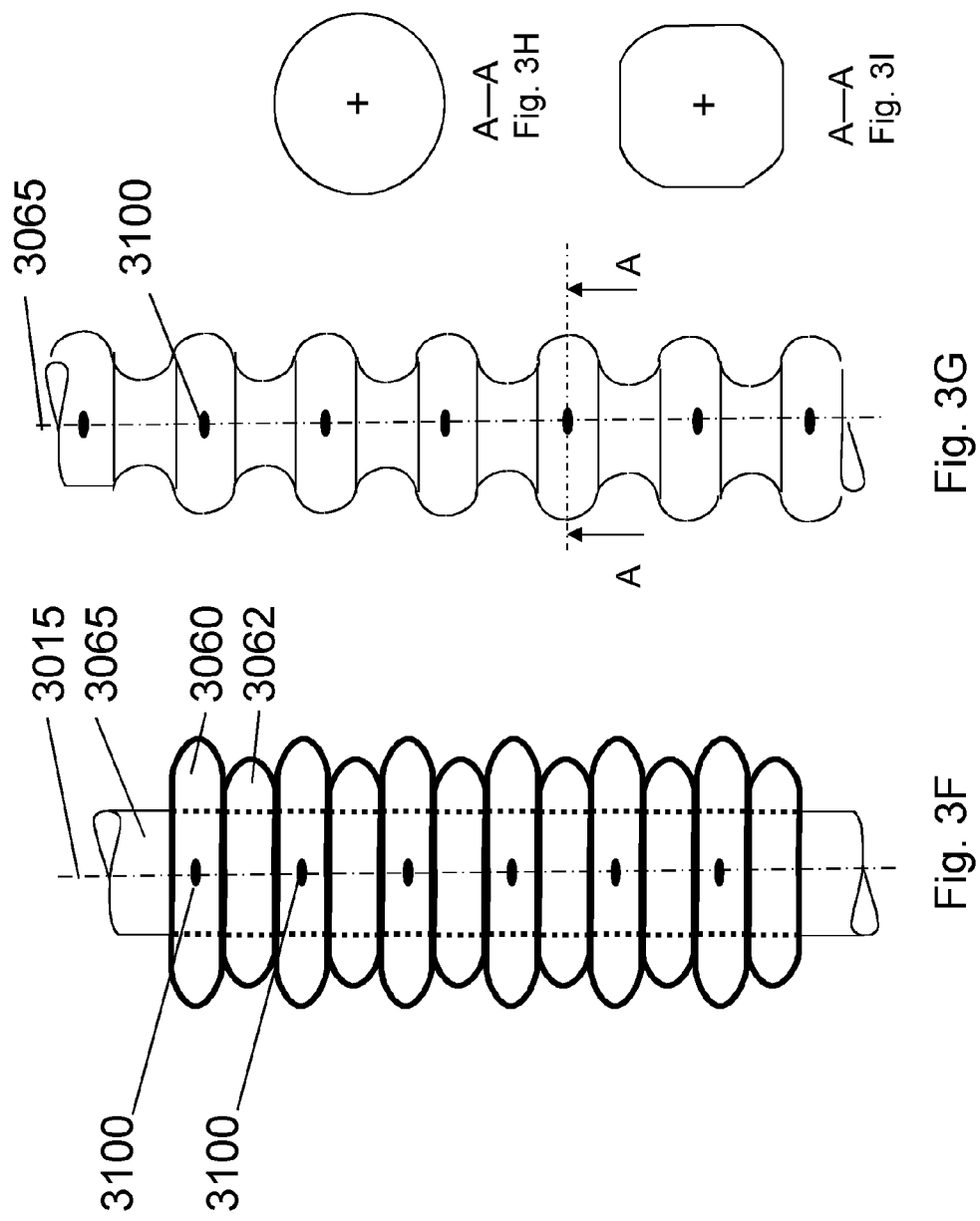

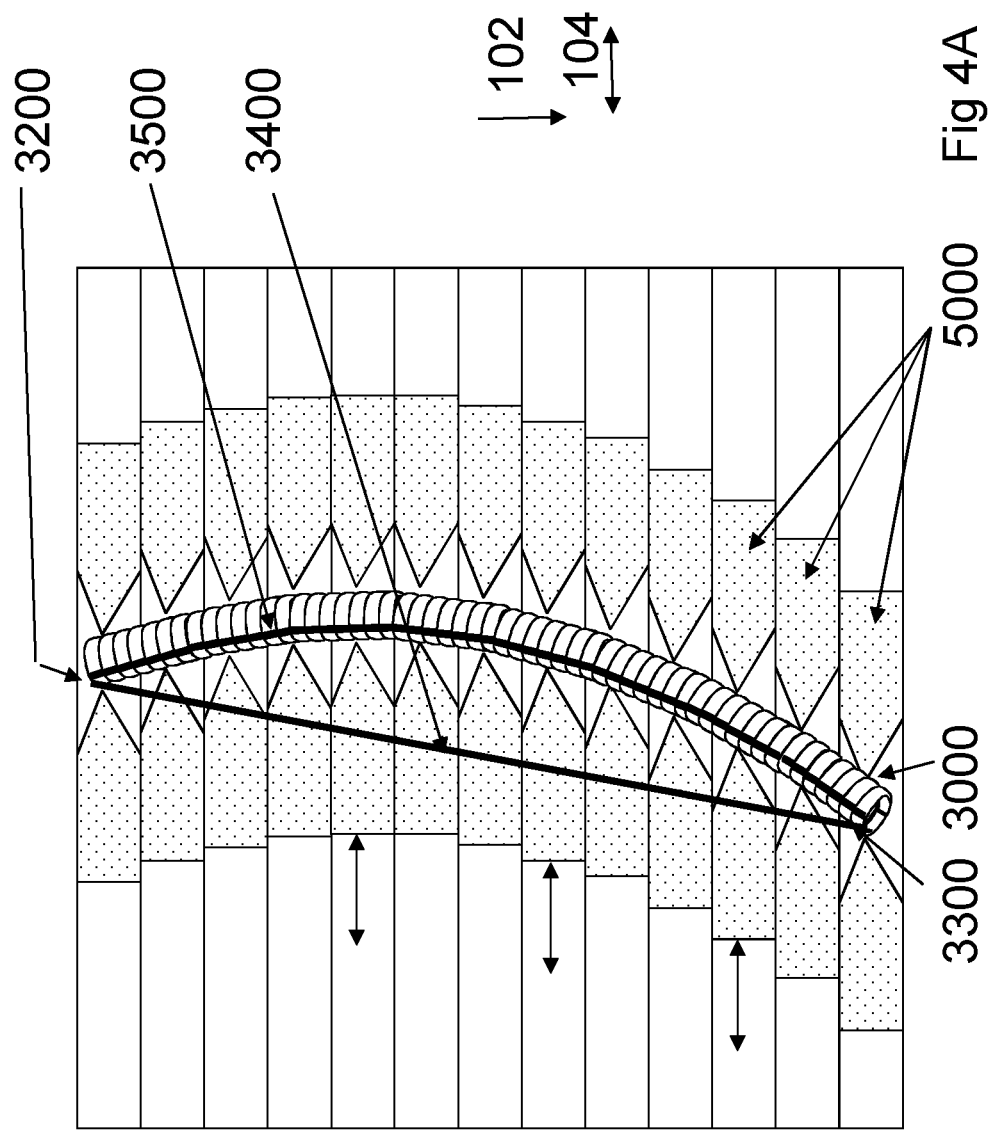

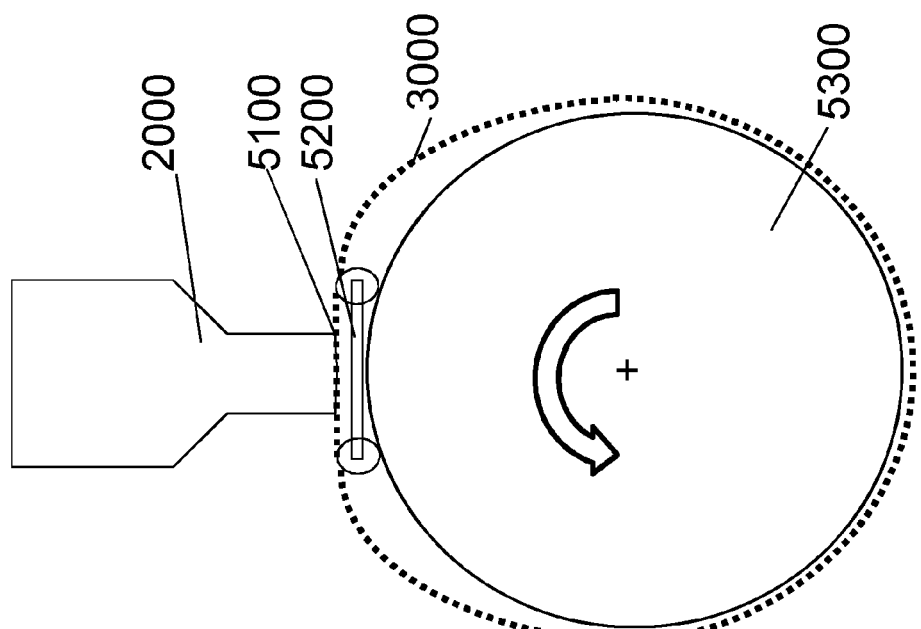
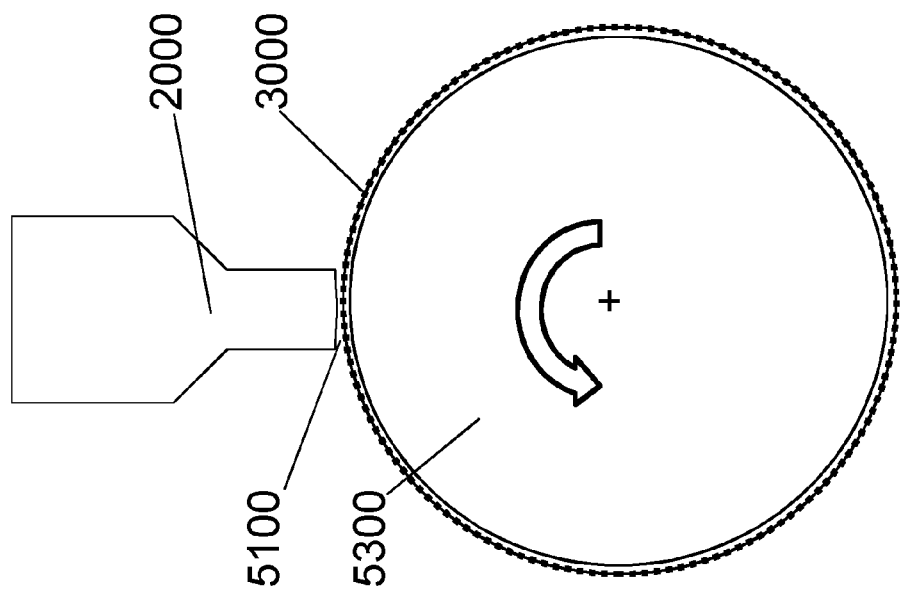

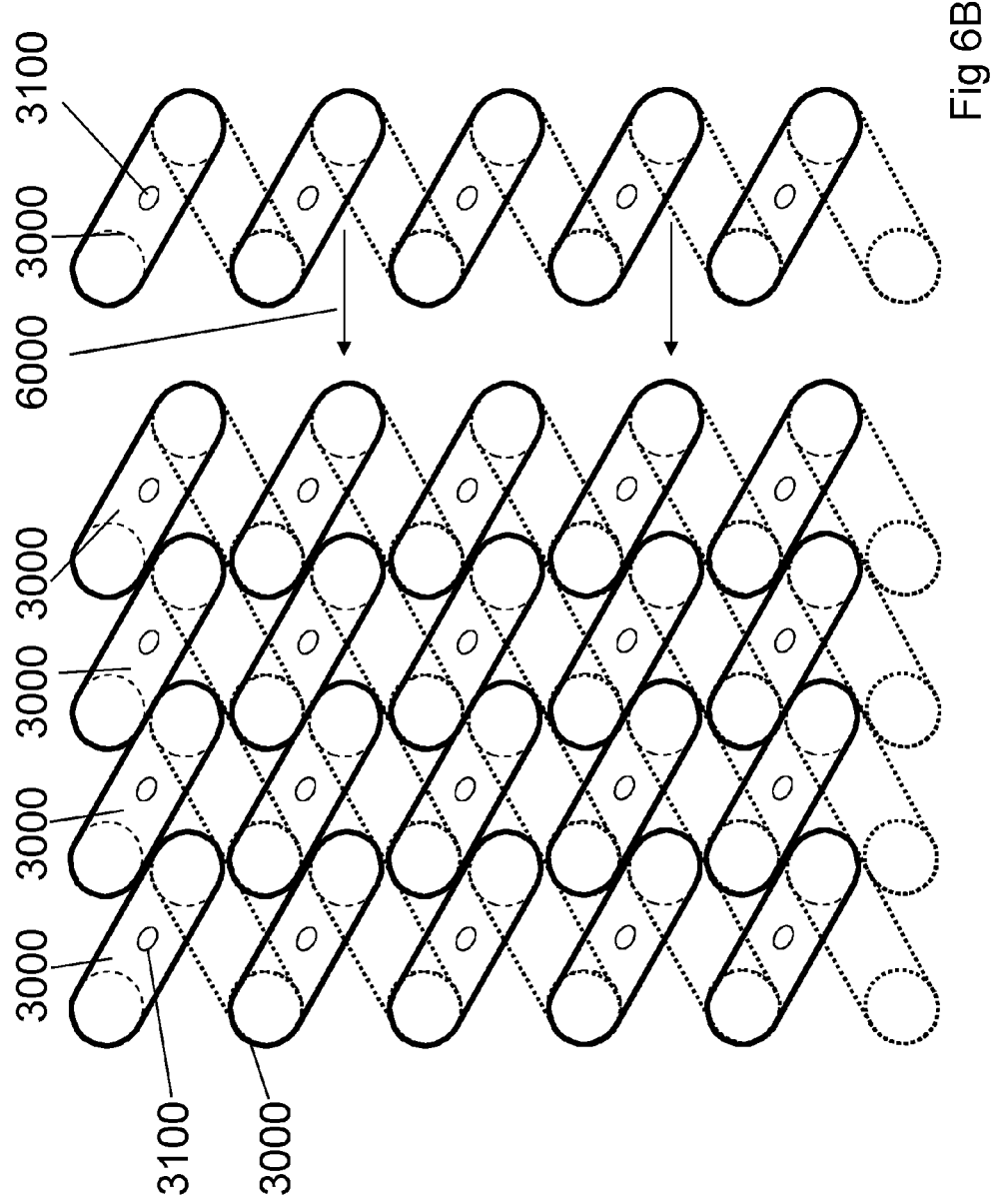

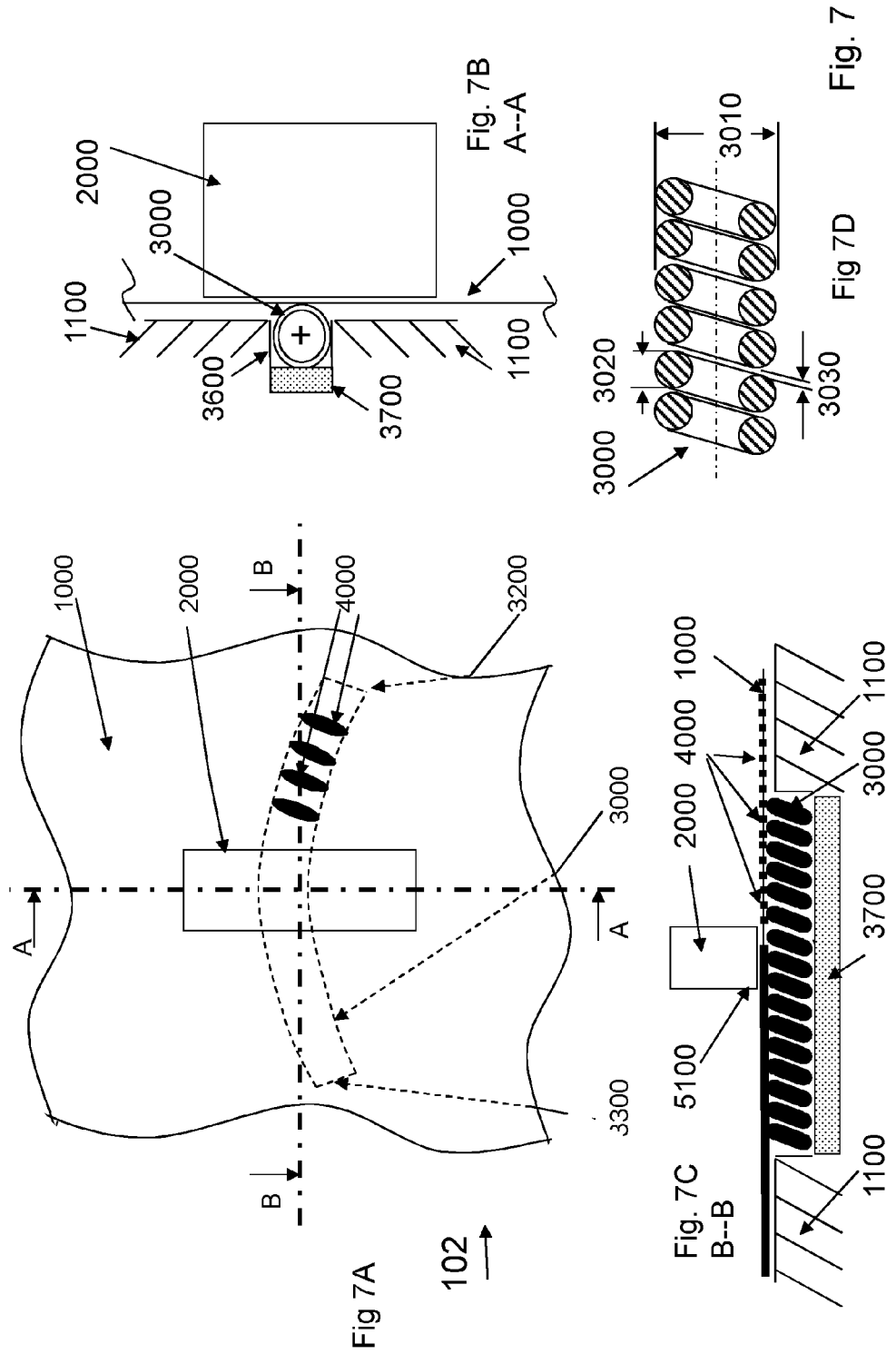

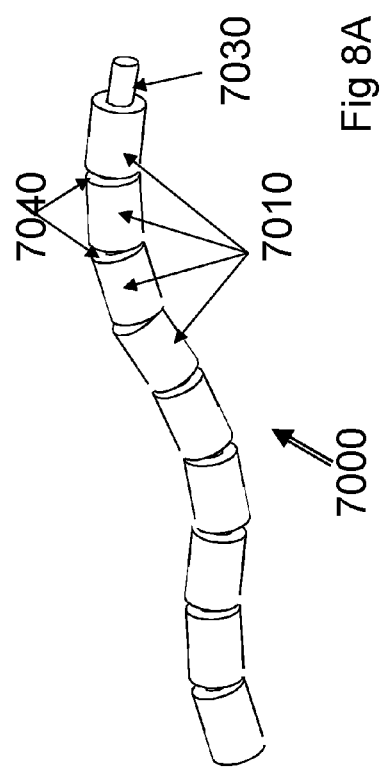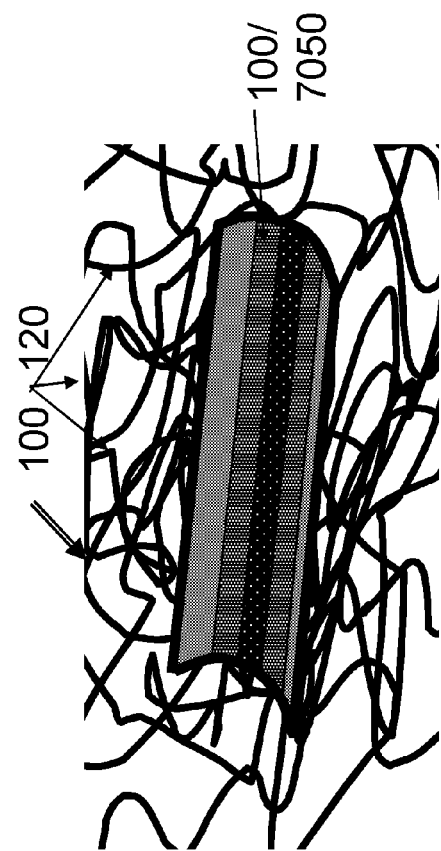

FORMING OF CONSOLIDATION REGIONS IN A WEB AND A WEB COMPRISING SUCH REGIONS

CROSS-REFERENCE TO RELATED APPLICATION

This application is the U.S. national phase of PCT Application No. PCT/EP2011/067203 filed on 30 Sep. 2011, which claims priority to GB Patent Application No. 1016533.0 filed on 1 Oct. 2010, GB Patent Application No. 1109418.2 filed on 6 Jun. 2011, and GB Patent Application No. 1113003.6 filed on 28 Jul. 2011, the disclosures of which are incorporated in their entirety by reference herein.

FIELD OF THE INVENTION

The present invention relates to apparatus and methods for thermally treating webs which comprise thermoplastic respectively meltable compounds, by creating consolidation regions which may optionally comprise an aperture, by employing a thermal energy source, such as ultrasonic energy, as well as to webs comprising consolidation regions. In a particular aspect, the invention concerns apparatus and methods for creating the elliptic consolidation regions by using a tubular anvil with circumferential ribs.

BACKGROUND

Treating webs which comprise meltable components with thermal energy is well known in the art, both for bonding such webs and/or creating apertures in such webs, such as by running webs through a nip of two rolls, one or both of which may be heated and/or embossed. This principle can be applied to consolidating webs as such, such as non-woven webs, or by connecting webs to each other, such as creating a seam-like bond.

For example, businesses in the textile and personal products industries often manufacture articles such as diapers, clothing, etc., that are ultrasonically welded.

U.S. Pat. No. 6,457,626 (Branson) describes the use of a rotary anvil and a rotary horn comprising two symmetrical halves, for ultrasonic welding of diapers, clothing in textile and personal products industries and film sealing industries. U.S. Pat. No. 6,517,651 (Tefron) describes a stationary ultrasonic horn cooperating with a rotating anvil. U.S. Pat. No. 6,517,650 (Kimberly-Clark) pertains to apparatus and methods for intermittently creating ultrasonic bonds in sequentially advancing work piece segments in a nip. The apparatus is designed sufficiently rigid, that the ultrasonic horn and the anvil can be brought together with low interference levels.

In EP1144187A1 a process is described, wherein circular protrusion on a bonding roll create circular bond points exhibiting a particular three-dimensional cross-section. However, the construction of such a roll as well as its operation is difficult and the circular bond points do not allow for directional property differences in the material.

In WO2008/129138 individual bonding points are shown having the shape of oval perimeter aligned in machine respectively cross-machine direction. According to the description it improves the abrasion resistance without compromising softness and drapeability.

WO99/014415 discloses a bonding pattern for a web showing oval bonding points arranged in a skewed angle relative to the machine direction. In WO09/021,473 (PEGAS) a bonding pattern is described with machine directionally extending bonding points. On the bonding roll, the bonding point protrusions have an oval shape and a trapezoidal cross-section. In U.S. Pat. No. 6,713,159 (K-C) a seaming pattern comprising oval bonding points is described. U.S. Pat. No. 6,220,490 (K-C) discloses a seaming pattern with at least two sub-patterns for specific distribution of stress forces across the seam. In U.S. Pat. No. 5,620,779 relating to creating ribboned non-woven, bonding patterns are described which comprise ovals and/or ellipses as well as skewing of bonding pattern relative to the machine direction.

It is also known to employ ultrasonics for the creation of apertures in web materials, such as described in U.S. Pat. No. 3,949,127 or U.S. Pat. No. 3,966,519, relating to nonwoven materials, or U.S. Pat. No. 3,756,880 relating to films.

It is characteristic of such known methods, that the total system of energy emitting source (e.g. sonotrode) and counteracting anvil is designed very stiff and rigid, as it is believed that flexibility in the system induces inaccuracy and is influencing the energy transmission.

SUMMARY

The present invention is an apparatus or consolidating one or more region(s) of one or more web(s), which comprise(s) thermoplastic material and which exhibit a length (x-), width (y-) and thickness (z-) direction, by plastic deformation. The apparatus exhibits an x- or machine direction aligned with the direction of movement of the web(s) relative to the apparatus, a y- or cross-machine direction aligned with the width direction of the web(s). The apparatus comprises one or more energy source(s) for increasing the temperature at least of the region(s) of the web(s), a first and a second anvil forming a gap and adapted to receive the web(s) therein such that the thickness or z-direction of the webs is aligned with the gap width, and a gap width adjustment means adapted to apply pressure to the web(s) in the gap. The first anvil comprises a x-directionally elongated flexible member which is flexible at least in its y- and z-directional first anvil support structure. Preferably, the flexible elongated member forming the first anvil has an x-directional extension which is at least twice as long as the average of its main cross-sectional distances. The flexible elongated member of the first anvil preferably exhibits a flexibility degree of more than 0.1 mm, preferably more than 0.2 mm, more preferably more than 0.5 mm, and further suitable materials may exhibit a value of more than 1 mm or more than even 1 cm. In a preferred execution, the flexible elongated member may comprise metal.

The first anvil support structure preferably exhibits hardness higher than the hardness of the elongated member and may be executed as a planar support or a cylindrical roll. In the latter case, the apparatus further comprising an anvil element lifting device positioned stationary relative to the gap and adapted to lift up portions of the flexible elongated member from the support structure in or adjacently to the gap region.

The apparatus may further comprise a damper element positioned between the elongated anvil member and the anvil support and exhibiting a flexibility which is higher than the one of the flexible elongated element and of the flexible element support. Preferably, the damper element exhibits a hardness less than both the elongated element and the first anvil support structure.

The flexible elongated anvil element may have an outer dimension/extension in y- and z direction of less than 80 mm, preferably less than 20 mm, more preferably less than 12 mm. At least a portion of the flexible elongated member is positioned on or recessed in the surface of the support structure.

The apparatus may further comprise a flexible elongated member shaping means adapted for y-directionally displacing predetermined portions of the flexible elongated member.

In a particular execution at least one of the energy sources emits sonic, preferably ultra-sonic energy. The flexible elongated member of the first anvil is selected from the group of
i) wires,
ii) chains being a series of connected elements, wherein the elements exhibit a flexibility which is lower than the one of the total chain and which are pivotally or inter-meshingly or inter-engagingly connected to form the chain), and
iii) tubular members with circumferential ribs.

The wires may have a spherical or elliptic cross-section, or have a hollow core and the chains may comprise cylindrical or frusto-conical elements lined up on a flexible core.

The tubular members with circumferential ribs may be selected from the group consisting of a helical spring, which may comprise a coil wire having a cross-sectional shape which is circular, elliptical, flattened spherical, or hexagonal, litz wires, shim rings mounted on a flexible core, and bellowed, corrugated, finned flexible tubes.

For certain applications, the coil wire may have an outer diameter of less than 10 mm, more preferably less than 5 mm, even more preferably less than 2.5 mm.

In a second aspect, the present invention is a web exhibiting a x- or machine direction, a y- or cross-machine direction, and a z- or thickness direction, comprising one or more consolidation region(s) with indentations, which have an essentially non-circular elliptic, rectangular or trapezoidal shape in the x-y-orientation of the web, and which have a cylindrical, ellipsoidal or frusto-ellipsoidal form. The web may be compressible and comprise fibres or foams, and may also form a composite with other webs, including films.

The major axis of at least one of the elliptic, cylindrical or frusto-conical consolidation regions in the web may be at an angle of more than 0° and less than 45° to the machine direction of the web. The consolidation regions may comprise apertures of predetermined size, such as straight or curvilinear slits. The consolidation regions may form a predetermined pattern wherein a plurality of consolidation regions are positioned along a consolidation pattern line. Optionally, the major axis of at least one of the consolidation regions is at an angle of more than 0° and less than 45° to the consolidation pattern line. The predetermined pattern may extend essentially over the full surface of the web.

The predetermined pattern may form a seam for connecting two webs or two or more layers of one web. When the webs are essentially water impermeable and the seam is essentially water impermeable exhibiting a water hydrohead of at least 80% preferably 90% of hydrohead of the web material having the lowest water hydrohead.

In a third aspect, the present invention is a method for creating a plurality of consolidation regions in one or more web(s), comprising the steps of
a) providing one or more web material(s) comprising thermoplastic material, the web(s) exhibiting a x- or machine direction, a y- or cross-machine direction, and a z- or thickness direction;
b) forming a gap corresponding to the z-direction of the web(s) between a first anvil with a flexible anvil element being supported by a support structure, and a counteracting second anvil,
wherein the flexible anvil element exhibits in the gap a z-directional flexibility which is higher than the corresponding one of the anvil element support structure;
c) feeding the one or more web(s) to the gap;
d) setting the z-directional gap width or the gap pressure between the second anvil and the flexible anvil element to a pre-determined level;
e) optionally providing energy to induce a temperature increase in the web or in predetermined regions thereof;
f) compressing the web(s) in a predetermined pattern in the gap, thusly creating the consolidation regions,
such that the consolidation regions exhibit an non-spherical ellipsoidal, frusto-ellipsoidal, cylindrical, or frusto-conical indentation in the web.

When the one or more webs exhibit fluctuations around a pre-determined target of at least one web property selected from the group consisting of basis weight, density, calliper, and composition, and the predetermined level of the gap width or gap pressure is set according to step d) corresponding to the pre-determined target of the web property, the flexibility of the flexible anvil element and/or of an additional damper element buffers the web fluctuation, such that the shape of the consolidation regions is essentially unaffected by the fluctuations.

BRIEF DESCRIPTION OF THE FIGURES

FIG. 1A to D show schematically views of consolidation regions according to the present invention in a fibrous web.

FIG. 2A to D show schematically a set-up as may be employed to practice the present invention.

FIG. 3A to I show schematically various executions of a tubular anvil element according to the present invention.

FIGS. 5A and B show schematically two executions for an equipment set-up according to the present invention.

FIG. 7A to D show schematically a set up as in FIG. 2A to D with the additional feature of a damper element.

FIG. 8A shows a schematic view of a further execution of an anvil element according to the present invention, and FIG. 8B schematically depicts a consolidation region as may be created with such an element.

Same numerals depict corresponding elements or features in all figures.

DETAILED DESCRIPTION

Figure 1A:
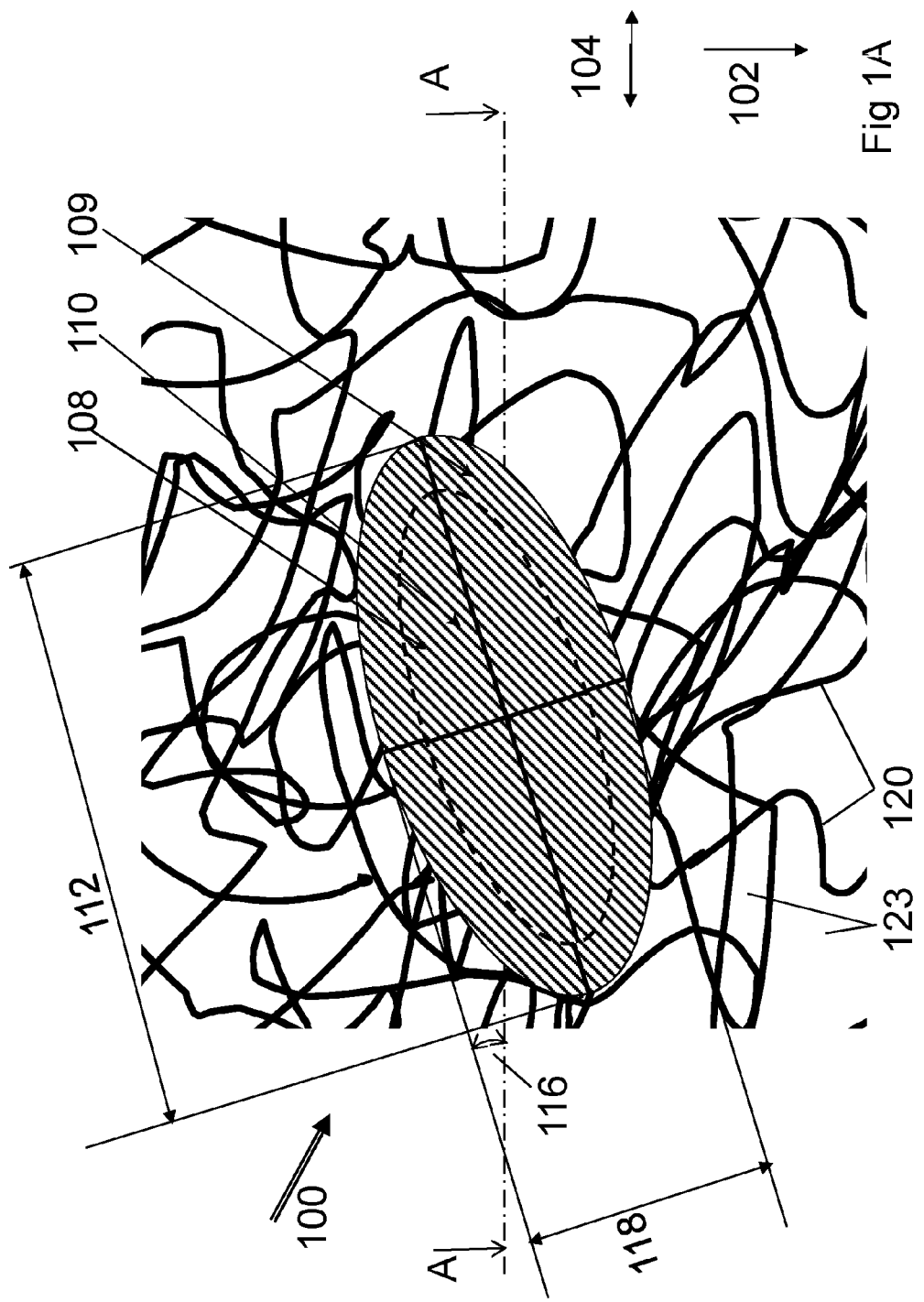

The present invention relates to the consolidation of one or more web(s). In a first aspect, the present invention is an apparatus to achieve such consolidation regions by employing an elongated flexible anvil element, which may be executed as a wire, a tube, or a chain, or as a tubular element with circumferential ribs. In a second aspect, the present invention is a process for creating a plurality of consolidation regions in one or more web(s), in particular when such a web exhibits fluctuations in its material properties. In a third aspect, the present invention is a web which comprises consolidation regions, which either have cylindrical or ellipsoidal.

It should be noted that the present description covers various execution of various features and elements, which, however, are not necessarily limited to the context in which they are described.

Within the present context, the term "web" or "web material" refers to materials, which—when employing Cartesian coordinates—exhibits a general longitudinal or x-directional extension, which may be and often is the direction of the material on a roll. In this direction, the web is essentially endless, or at least significantly longer than in its width or y-direction perpendicular thereto. The web has a thickness z, typically much smaller than either of the x- or y-direction. Web materials may be essentially solid materials, such as in the case of film or foils, or may have porous regions and be readily compressible, such as in the case of fibre containing materials, or foams, or when films are three-dimensionally formed. A web may be a combination or a composite of several materials, such as when two or more layers of material are combined. The layers may be other webs, or may be material pieces, such as may be cut pieces from other webs.

When a web comprises fibrous materials, these may be bonded webs, such as nonwoven webs, or may be batts, such as an unbonded accumulation of fibres, or may be an accumulation of several strata of fibrous material. Such batts may also comprise a certain amount of bonding between the fibres. Webs may be bonded or pre-bonded by any conventional technique, such as by heat- or melt-bonding, which may be created through compression and/or application of pressure, heat, ultrasonic, or heating energy, cohesion, adhesion, such as by glue or adhesive application. Nonwoven webs can be formed by many processes including—without limitation—meltblowing, spunbonding, spunmelting, solvent spinning, electro-spinning, carding, film fibrillation, melt-film fibrillation, airlaying, dry-laying, wetlaying with staple fibers, and combinations of these processes as known in the art. When the web comprises films, this refers to essentially continuous layers or strata of skin- or membrane-like material, though such films may also comprise apertures, or may actually form a net-like structure.

The present invention relates to consolidating a web. Thus, a web according to the present invention comprises thermoplastic material, i.e. meltable or at least softenable materials or compounds, which have a melting temperature higher than an ambient temperature of 25° C., but typically less than about 300° C. Typical materials may be—without limitation—polyolefins such as polyethylene or polypropylene.

Webs according to the present invention may further comprise other materials, such as particulate material, or fluids applied thereto, as long as the web-structure is not compromised. The web may comprise further materials, which are not thermoplastic, i.e. non-meltable, such as without limitation cellulosic fibres, or which melt at higher temperatures. The amount of meltable material will determine the properties of the resulting web, and for most applications, the web will comprise at least 10%, often more than 50% or even more than 90% of the meltable components.

A web can be a single layer web, e.g. when a pattern is introduced thereto. A web can be a single folded web, e.g. when edges are overfolded and seamed. A web can be made up of several individual webs or strata which are to be connected according to a preset pattern.

A web typically exhibits certain variations of its properties along its machine and cross-machine direction. A lot of effort is often spent against homogenizing such variation, such as by overlaying several sub-strata. However, important properties, in particular basis weight, density, calliper, and in the case of fibrous materials fibre diameter, fibre distribution (homogeneity) fibre length etc. still vary to a certain degree, and thus often provide difficulties in the further processing of such a web, in particular when such a web is combined with other materials, such as by fusion bonding. Typical issues are incomplete consolidation or "burn through", i.e. an undesired hole is formed in the bonding region.

In view of the present discussion, it should be noted, that the term "variability" refers to parametric values of the respective property as determined by any appropriate measurement method with a resolution that allows differentiation between the consolidation points and the circumscribing regions of the web. Express reference is made to the 2011 edition of the Standard Test Methods for the Nonwovens Industry issued by EDANA, Brussels, Belgium. Within the present discussion, a web comprises one or more consolidation region(s). A consolidation region is a web region which was subjected to a thermal and/or mechanical treatment, whereby at least a portion of the web material is softened or melted and subsequently or simultaneously compressed so as to create a plastic deformation of the material. A typical example well known to a skilled person is a thermoplastic fibrous material, which is bonded to become a bonded nonwoven material by introducing consolidation regions, often also referred to as bonding points, such as may be achieved by running the unbonded batt though a nip between two heated rolls, at least one of which has bonding protrusions, which will create a corresponding bonding pattern in the web. Another typical example is the seaming of two materials, such as well known in the making of disposable articles, where two webs, such as a non-woven web and a plastic film, are bonded to each other such as by applying pressure and/or thermal energy.

In the consolidation regions, the thermoplastic meltable material is molten or at least sufficiently softened so as to allow plastic deformation. In this consolidation region, the web material is compressed so as to exhibit a smaller calliper or thickness than the surrounding region. If the web essentially consists already of solid molten material, such as may be the case with film material, also these may be compressed, such as in the case of embossed films or in the case of two films being bonded together. Otherwise, a small amount of the film material may be squeezed laterally outwardly. Around a centre region of the consolidation region, where this plastic deformation and reduction of calliper or thickness occurred, the consolidation region comprises a transition region, as a transition from the centre region to the surrounding region of the web, which is not being consolidated the same way as the consolidation region. In this transition region, the thickness/calliper of the web increases from the centre region to the surrounding region, whilst the local density decreases accordingly. Some of the molten or plastically deformed material may be squeezed from the central region into the transition region.

The consolidation region exhibits a certain geometric extension, both with regard to the x-y-dimensions of the web, as can be seen in a x-y-top view of the web and to the z-directional dimension, as can for example be seen in a cross-sectional cut along the thickness direction of the web. It is a particular feature of one aspect of the present invention that the consolidation regions in the webs have a particular shape.

In one execution of the aspect, the consolidation regions exhibit a generally non-circular elliptical shape in their top view and that also the x-z- or y-z-oriented cross-section through a consolidation point exhibits at least partially elliptically shaped boundaries. The latter corresponds to an ellipsoidal or frusto-ellipsoidal indentation in at least one surface of the bonding region, which may be formed of the centre region and the transition region. The smooth transition from the consolidation region to the surrounding regions provides a particular balance of tactile properties and strength. The major or longer axis of the ellipse may be aligned with any major direction of the web, though in a particular embodiment the axis may be at an angle of more than 0° and less than 45° to the machine directional axis of a web. Within the present context, the term "frusto-ellipsoidal" refers to a shape of a truncated ellipsoid, i.e. an ellipsoid of which a part is cut away by a plane. Whilst geometrically strictly speaking also circles represent a special form of an ellipse, they are not considered within the present scope, as these will not provide particular benefits as will be discussed in more detail herein below. Thus the term ellipse should be read as non-circular ellipse.

In a second execution of this aspect, the consolidation regions exhibit a cylindrical indentation with an essentially rectangular shape in their top view. It should be noted, that in a preferred execution this cylindrical shape corresponds to a right circular cylinder, though non-circular, non-right-angled, and even cylinders with a apex (i.e. having a frusto-conical shape) are considered to fall within the scope of the term cylinder. In this execution and in contrast to the previous execution the smooth transition from the consolidation region to the surrounding regions is effective only in the radial direction. For certain applications, this may provide an even wider range of balancing properties.

Typically, though not necessarily, several consolidation regions form one or several readily recognizable repeating pattern(s). Therein a row of regions is a group of regions that are arranged predominantly along the cross-direction, whilst in a column the group of regions is arranged predominantly along the machine direction. Within the present description, "predominantly" refers to the situation, that the projection of a characteristic line onto one direction is larger than onto the other direction perpendicular thereto. There may be more than one pattern simultaneously in one web, which may be intermittent, overlaying, inter-digitizing. Such patterns may be formed simultaneously, and thus typically are in a specific registry to each other. Such patterns may also be formed independently of each other and then often have no direct correlation to each other, such as when a web already having a bonding pattern is submitted to a process according to the present invention, or if a web is treated twice in subsequent process steps according to the present invention.

In a first embodiment, the molten material is partly removed from the consolidation region, such that effectively a predetermined weakening of the web or even a hole or an aperture can be achieved. In contrast to the above mentioned "burn through", this aperturing can be achieved in a very reproducible manner, such as when a predetermined aperture size is desired. The aperture may also be an essentially endless one, such as for separation of the web.

In a second embodiment, the molten material remains in the consolidation region, which is then often referred to as a "bond point" or "bonding region". Such a bond point may be used for bonding or consolidating components of such a web, such as when the untreated web or batt comprises loose fibres. Also, bonding may be performed between strata or layers of one or more webs, such as when spun-laid or melt blown layers are positioned on each other, bonding can be achieved across all or some of these layers or strata. Similarly, bonding may be achieved between two or more webs, which may differ in at least one property, such as a film and a fibrous web. Further, the process according to the present invention may create an aperture in one of the layers but a bond point in one or preferably two enveloping webs.

In particular for the bonding of fibre containing webs, the process according to the present invention provides improved tactile softness. Without wishing to be bound by the theory, it is believed, that this improvement results from the gradual transition of a fibrous structure around the consolidation regions to the molten centre of the regions.

The consolidation regions are formed by passing the web(s) through a gap, formed by a first and a second anvil, such as—without limitation—the nip between two essentially cylindrical rolls.

Often, the gap is described to be between a tool and a counteracting anvil, indicating that on one side of the gap a certain action is performed, whist the other side of the gap is passive. Within the present context, such a distinction does not appear appropriate, and henceforth either side of the gap is referred to as an "anvil". Within the present context, the first anvil comprises at least one flexible elongated anvil element, as will be discussed in more detail.

The second anvil may be a cylindrical counter roll having a roll axis aligned with the cross-machine direction of the process and the web. Conventional thermo-bonding equipment often comprises a smooth anvil roll and a patterned embossing roll. The pattern is created by protrusions on the surface of the embossing roll. Typically, such protrusions exhibit a frusto-conical or frusto-pyramidal shape, or a trapezoidal cross-section.

The second anvil may be heated, or may comprise energy emitting elements, such as ultrasonic devices. Accordingly, also the first anvil may have heated elements, or may have (in addition to having the flexible tubular anvil element) protrusions.

The gap has a gap width, which extends in the z-direction of the web, and which is the narrowest distance between the anvils in the gap. Thus, if a gap is formed between a smooth and an embossed roll with protrusions, the gap width is the distance between the top of the protrusions and the smooth roll. If the protrusions have a rounded surface, the gap width is between the top of the curvature, which is oriented towards the smooth roll, and the smooth roll. The gap width impacts the compression in the consolidation regions, such that upon reduction of the gap width apertures may be formed therein. The gap width together with the height of the protrusions also determines, if a web run through the gap is not compressed, or only compressed to a certain degree outside of the consolidation regions. If one or both of the anvils have a round shape, such as when cylindrical rolls are used, the gap extends along a cross-directionally oriented line, defining the gap region.

In order to create consolidation regions, energy is applied to the web. A thermal energy source may be any heat source as well known in the art for thermo-fusing web materials. It is also contemplated, that the energy is provided by several means. For example, the web may be pre-heated to a temperature close to the plasticizing or melt-temperature before it is run through a nip, where by mechanical deformation energy through the pressurizing in the nip and/or additional thermal energy—such as by heated protrusions—the material is plasticized or molten, such that upon compression consolidation regions are formed.

In a preferred execution, an energy source in the second anvil creates sonic, more preferably ultrasonic waves. Ultrasonic welding tools operate under the principle of applying acoustic energy in the ultrasonic frequency range (i.e., typically at or above 20 kHz) to a horn. The horn or sonotrode vibrates in response to the applied acoustic energy to further produce an output acoustic energy. The output acoustic energy is applied to the thermo-fusible web materials which are positioned between the sonotrode and a counteracting support, respectively anvil. The vibration energy travels through the web, and is converted to heat. Without wishing to be bound by the theory, it is believed that the conversion is due to intermolecular friction that melts and fuses the thermo-fusible material such that it can be fused by compression.

The thermal energy source is preferably positioned stationary relative to the moving web and anvil, but it may also be rotatably mounted and optionally also translatorily moveable. Preferably the one or more thermal energy source(s) are designed sufficiently wide to cover the full y-directional extension of the bonding curve or bonding area to avoid or minimize y-directional movement of the energy source.

The anvil or anvils comprise surface elements forming the gap and form the consolidation regions in the web. The anvil or the anvils may further comprises means for maintaining the positioning of webs hereon, such as vacuum suction means.

These consolidation regions will then "imprint" the surface elements into the web. Thus, a pattern of the anvils can be seen as a pattern in the treated web. However, the pattern will not be mirrored exactly in a one to one relationship. The relative positioning of centre points of protrusions may be about the same as of the centre points of the consolidation regions, depending e.g. on longitudinal and cross directional extension of the web, but the size of the consolidation regions may differ from the size of the protrusion. The difference in size is primarily depending on the shape and form of the protrusions cooperatively with the gap width, gap pressure, and material calliper.

Thus, if the protrusions were cylindrical and had a rectangular cross-sectional shape along the surface of their support, the centre region of the consolidation regions should have for a sufficiently small protrusion depth the same size and shape as the protrusions. As commercially used bonding tools typically comprise protrusions that exhibit a trapezoidal cross-sectional shape when viewed along the surface of their support, this will for example result for a greater penetration depth or smaller gap width and a given material in a larger consolidation region, as even if the centre region of the consolidation region remains the same, more material will be squeezed into the transition region which will thusly be enlarged. However, the sharp angle between protrusion top and side surface will create a small transition region with a sharp change in properties, where fibres and/or fibre anchoring may be damaged, thusly resulting in reduced strength of such conventional webs.

Further, for a given protrusion shape the gap width or gap pressure will impact the penetration depth of the protrusions into the web, and the molten material will be squeezed to a different degree laterally outwardly into the surrounding, depending on the calliper of the material. Thus, the centre region of the consolidation region may correspond to the protrusions, but typically will be somewhat larger by having some of the molten or plastically deformed material into the transition region.

These effects are much less pronounced in the technology of the present invention, compared to the described conventional ones: As the flexible elongated anvil elements slope away from the "highest" contact point in one direction in case of the cylindrical indentations and in all directions in case of the elliptical indentations, there is effectively not one penetration depth, but the cylindrical or elliptical indentations as described will result. Because of the sloping of the protrusion molten material is displaced from the deepest impression point in the centre of the centre region towards the less deep impressed regions of the centre region and possibly into the transition region. Thus a much more gradual transition will result with less fibre damage and henceforth improved strength, whilst having a much smoother boundary and hence improved tactile softness.

As described in the above, any web material exhibits certain variability with regards to certain important web properties, such as basis weight, density, or calliper (which may be interdependent), but also fibre diameter, fibre distribution etc in case of fibre containing webs or pore size and lamellae properties in case of foams. Thus when such webs are run though conventional processes such as thermo-bonding or ultra-sonic bonding, the process is susceptible to such variability, and an unstable process may provide unacceptable variability in material properties, such as incomplete melting, "burn through" etc, all well known to a skilled person. Accordingly, significant effort has been spent for conventional stiff and rigid systems against adjusting the gap width according to such variability, such as described for the case of applying ultra-sonic energy to a web, e.g., as described in EP0920977A1 (Herrmann).

In contrast thereto, the present invention exploits the flexibility of the elongated anvil elements. In this, the present invention relates to an apparatus for creating one or more consolidation region(s) by plastic deformation in one or more webs, which comprise(s) thermoplastic material. The apparatus exhibits a x- or machine direction aligned with the direction of movement of said web(s) relative to the apparatus, a y- or cross-machine direction aligned with the width direction of the web(s). The apparatus comprises one or more energy source(s) for increasing the temperature at least of predetermined regions of said web(s).

This temperature increase may be for the whole of the web, such as when the web is pre-heated, such by being run through an oven, or over heated rolls, or by radiation, or by hot air forced through the web. Preferably, the heating is not limited to the heating of the surface, but the temperature is increased homogeneously throughout the web.

The temperature increase may also be for predetermined regions only, such as when protrusions of a heated roll contact the web. The energy source may also be integral with the compression unit, such as when mechanical energy is transformed into thermal energy.

The apparatus further comprises a first and a second anvil, forming a z-directionally oriented gap exhibiting a gap width aligned with the z-(thickness) direction of the web(s). In the gap, pressure may be applied to the web by conventional gap width adjustment or pressure or force control means.

A first anvil comprises an x-directionally elongated flexible anvil element. The flexible anvil element is supported by a support structure, such as may be e.g. a planar support or a cylindrical drum. The first anvil cooperates with a counter-acting second anvil.

Within the present context, the term "elongated member" refers to an element, which has an x-directional extension which is larger than the average of the shortest and longest main cross-sectional distances (e.g. diameter). It is, however, contemplated, that also relatively short members may be employed, at least in combination with other, longer members.

The term "flexibility" refers to a property of the elongated member, which also may be referred to as flexural strength, and as such may be determined by methods known to a skilled person. Within the present context, the flexibility is determined by the flexibility test method.

In order to execute the flexibility test, the elongated member is firmly fixed (e.g., clamped) horizontally such that at least 5 cm protrude freely outwardly. At 5 cm distance from the fixation, a weight of 1 kg is applied and the vertical deflection is measured. It may occur, that the flexible member is so flexible, that it satisfies the deflection criterion without any or with a lower weight. If the elongated member is applied in the apparatus in a tensioned state (e.g., a tensioned spring), it should be measured in a relaxed condition. If the elongated member is of a chain type, the chain elements are typically very stiff and the flexibility of the chain is dominated by the flexibility of the pivoting joints.

A material is considered to be flexible, when it passes the flexibility test by exhibiting a vertical deflection in the test of more than 0.01 mm. Preferably, the material deflects more than 0.1 mm, more preferably more than 0.3 mm, and further suitable materials may exhibit a value of more than 1 mm or more than even 1 cm. It should be noted, that the flexibility test requires the deflection criterion to be satisfied in two directions perpendicular to each other and to the elongation axis of the member. The skilled person will readily realize, that other test methods such as ISO 12135 (Metallic materials. Unified method for the determination of quasi-static fracture toughness), ASTM D790 (Standard test methods for flexural properties of unreinforced and reinforced plastics and electrical insulating materials), ISO 178: Plastics—Determination of flexural properties) aim for determining essentially the same property, and thus may be employed equivalently, if the correlation is ascertained.

In a preferred execution of the invention the flexible anvil element exhibits a flexibility which is higher than the one of its support structure. Hitherto it has been believed that in order to provide good and uniform creation of consolidation regions, all parts of the equipment need to be sturdy and rigid, and any deformation should be minimized unless specific countermeasures are to be taken. Thus, heated calender rolls are often designed and manufactured towards minimal deformation, or ultra-sonic equipment has essentially undeformable anvils and complicated measures are taken to adjust the gap width upon material variability and/or process variability, such as temperature increases during operation.

The elongated flexible member preferably exhibits a certain resistance against mechanical stress, such as abrasion. Thus, the material, or at least the surface of the member exhibits a sufficient hardness, and in a preferred execution, the flexible member is made with or from metallic material, such as—without limitation—iron, steel, aluminum, or mixtures or composites thereof.

Within the context of the present invention, the flexibility of the flexible member may result from its inherent material properties, such as by employing steel types having certain e-moduli. Preferably, and providing a much wider ranges of flexibility, the flexibility results from the internal structure of the elongated member Thus, in a first execution, the flexible member is a wire, which exhibits essentially constant cross-sectional dimensions over a large length, such as a simple iron wire, e.g. having e.g. a circular diameter of 2 mm and exhibiting a deflection of more than 1 mm when submitted to the flexibility test. Suitable wires may, of course, exhibit cross-sections of different shapes, such as elliptical, polygonal, star-like, crescent shaped and the like. Preferably, however, the wires have a shape such that a rounded surface can be positioned towards the gap. Within the present context, also tubes are considered as "hollow wires".

In a second execution, the flexible member is of the chain type, i.e. it comprises a series of connected elements, wherein the elements exhibit a flexibility which is lower than the one of the total chain and which are pivotally or inter-meshingly or inter-engagingly connected to form a chain A first example of such a member is depicted in FIG. 8A, showing cylindrical chain elements connected by a connecting element running through the core of the cylinders. In yet a further execution, the flexible element is a tubular element with circumferential ribs. This is further explained by considering a coil spring as a non-limiting example for such a tubular flexible elongated anvil element. The coil spring may be made from a type of steel having a modulus of elasticity which is lower than the one of the support. However, the particular shape of the coil spring provides a much higher flexibility than the wire of the coil as such. Without wishing to be bound by the theory, it is believed that this is due to the following reasons. First, considering the arched structure of a wire turn, this may transmit the forces tangentially away, and some reversible deformation may deform for example a circular wire into a somewhat elliptic one when the compression occurs. Even further, neighbouring turns may move relative to each other. Thus, the system exhibits a particular robustness with regard to variability, as it can react differently for each and every consolidation region. This combined effect is believed to result in a significantly smoothed operation, and peak forces are buffered away.

Optionally, and particularly beneficial in the context of an ultra sonic energy source, the flexible tubular anvil element and the support, both of which may be executed as described in the above, may be separated by a damper element, which is even more flexible or more elastic than the tubular anvil element. The damper element may exhibit the required flexibility or elasticity isotropically or uni-directionally. The flexibility or elasticity may be reached by inherent material properties, or by structural features, similar to the ones as described in the context of the tubular flexible element. Such a damper element may be an elastic, a viscoelastic, a viscous, or an pseudoelastic element, and may comprise natural or synthetic rubber, rubber-like materials such as SBS, SIS, (block-)copolymers, EVA, nylon, or silicones, or thermoplastic elastomers, mastics, asphalt based or bituminous material. The damper element may comprise cellulose based materials, such as paper or wood materials. The damper elements may comprise solid, foamed or sponge-like, fibrous or shim-type structures, and voids or interstices thereof may be filled with another material.

Without wishing to be bound by a theory, it is believed, that as long as deflection behaviour such as a reaction to the vibration of the ultrasonic energy source, which can be described by the moment of inertia of the flexible tubular element and the buffer element are such that the damper element is not vibrating with the frequency of the ultra-sonic source, and preferably also not with a resonance frequency of the ultra-sonic energy source (typically in the order of magnitude of 20 to 35 kHz), the ultrasonic energy will be transferred to the material in the gap and the flexibility or elasticity of the tubular element and the damper element allows broadening of the process tolerance (window) such as with regard to material thickness or basis weight variations, but also with regard to varying distances of the support element to the energy source, such as may result from unbalanced rotation in case of the support structure being a rotating drum or turret. It should be noted, that equivalent executions for such a damper element are included within the scope of the present invention, such as when the damper element is executed integrally with the support element, or if the damper element comprises multiple individual sub-elements, each individually or jointly satisfying the above requirements.

In addition to the flexibility in view of reacting to compression in the gap, the flexible elongated element is preferably executed such that it can be easily deformed along and perpendicularly to its longitudinal axis, i.e. the centre-line of the tubular anvil. Whilst this is an important feature of all executions of a flexible elongated member, the following discussion will use the third execution of a tubular element with circumferential ribs as an exemplary element, and even more specifically a coil spring. This is considered a preferred execution for many applications, though the following description of the effects should not be seen to limit the present invention. If such a coil spring is laid on a x-y-surface, such as of a support structure, with its axis being predominantly oriented in the x-direction, the spring can be easily deformed and bent in the y-direction. The axis will then become a curved axis, and the turns of the spring will remain essentially at the same angle to the axis as before the y-directional curvature occurred. Depending on the curvature, neighbouring wires may become to a certain extent distant in one side of the curve, whilst they may come in contact or remain in contact on the other side. Further, the flexibility may also relate to the length of the tubular anvil element, as such a spring may be readily extended without losing the overall structural shape. The wire of the coil may also show a polyangular cross-section, such as a rectangle, triangle or a hexagon.

Such a flexible elongated tubular anvil element with circumferential ribs can be constructed by various ways, such as when mounting shim rings of two different outer diameters alternating on a flexible core, such as made of elastic material. The larger shim rings form the circumferential ribs, and the smaller shim rings define the spacing. Another suitable approach is the use of bellowed, corrugated, or finned flexible tubes, as well known such as for compensation tubes. A preferred embodiment is a coil spring, as will be described in more detail herein below.

In addition to the mechanical benefits of a flexible elongated anvil element, it is believed, that it further provides advantages at high process speeds and/or when operating at very small gap widths, as the curved upper surface and the open structure allow for a very smooth air flow.

The size of the flexible elongated tubular anvil element may vary over a wide range, for many applications in the hygiene or packing industry the largest outer diameter of the circumferential ribs will be about 20 mm, and the length of the ribs, such as the thickness of the shim rings or fins, or the diameter of a coil spring wire, will be less than about 10 mm. In a particularly preferred embodiment the flexible elongated tubular anvil element is constructed by using a helical or coil spring, i.e. a helically wound wire.

A helix is a three-dimensional curve that turns around an axis at a constant or continuously varying distance while moving parallel to the axis, such as well known coil spring, i.e. a spring which can be made by winding a wire around a cylinder. Generally, such helical springs can be made and used as compression springs which are designed to become shorter when compressed along their length direction. Their turns (loops) are not touching in the unloaded position. Tension or extension springs are designed to become longer under a pull force along their length direction. Adjacent wire turns (loops) are normally touching each other in the unloaded position. Such a helically wound wire is defined by the inner and outer diameter of the helix (or coil), the form of the wire, the diameter of the wire (particularly when the wire has a circular cross section), the pitch (i.e. the distance of the centre points of adjacent wire turns), the canting angle (i.e. how much the connecting line of two adjacently opposed wire cross-section centre points is inclined versus the axis), and the hardness, stiffness and composition of the wire material, particularly at its outer surface. Typically, such helical elements show a circular cross section, but non circular cross sections such as e.g. elliptical ones may be desirable for particular applications. This also applies to the wire forming the helix, which may have a circular, a elliptical, or segmented cross-section, i.e. a circular or elliptical cross-section of which one or more segments are removed—either at the top surface (i.e. oriented towards the web(s)), and/or at one or both sides (i.e. oriented towards neighbouring wires).

Considering such a primary or first order structure of a straight helical anvil in Cartesian coordinates, the length or x-axis corresponds to the helix axis, whilst the y-direction is considered as width direction and the z-direction of thickness or height. Preferably, neighbouring wires forming the helix are displaceably contacting each other. Preferably the wire has a rounded wire cross-section, more preferably elliptical, most a preferably circular one. Alternatively, a part of the surface may be flattened, such as by being filed off, or the wire may have an oval or half-oval cross-section. Typically, the wire is solid, but provided the required mechanical properties are met, it can also be executed as a hollow tubular wire, optionally further comprising a core material. A wire may actually also be formed in the form of a helix (i.e. a "zero order helix"), optionally being wound around a flexible core, such as a hexagonal core. Any of the helical structures may be right- or left-handed.

Optionally the flexible elongated member can be made from a primary helical anvil structure formed by a secondary helical anvil structure, e.g. when a long circular spring is wound around an anvil drum. Adjacent primary structure elements may be contacting each other or even interfere with each other, such that effectively the total anvil drum surface may be covered by the primary helical structure, or they may be spaced apart from each other. Such a set up can be very advantageously used for example when a wide web is to be consolidated over its entire surface, e.g. to form a nonwoven web. In a further particular execution, two or more helices (respectively parts of one helix, which may be wound around a cylinder) may be positioned adjacently to each other in a staggered or interdigitating arrangement.

A further particular execution of helical anvil structure is a litz wire, illustrating the broad range of helical materials with regard to size of bonding points as resulting from small diameter strands, also with regard to a high area density of bonding points as may result from the high number of strands, and a high flexibility as being a typical characteristic of litz wires.

After having described particular executions for the flexible elongated member the following will again refer to particular executions as may be optional or preferable for the flexible elongated member as such.

Preferably the flexible elongated member is made of metal, although other materials satisfying the mechanical and inertia requirements and exhibiting appropriate thermal conductivity may be equivalently employed.

The flexible elongated member can have a straight axis. Alternatively, such as when the anvil is mounted on a drum like anvil support, the anvil axis may have the form of a circle on the surface of the anvil support. Also, the axis may be curvilinearly shaped in any dimension, such as when a spring is bent.

The skilled person will readily realize that the geometry of the flexible elongated member determines the geometry of the consolidation regions. Whilst no one to one translation of the dimensions will be possible, for example the wire gauge of a helical anvil having its axis predominantly along the longitudinal direction of the web will correspond primarily to the x-directional extension of a consolidation region, whilst the helix diameter determines primarily the y-directional extension.

In a first execution, a linear length of a flexible elongated member may be positioned in a flat anvil frame opposite the sonotrode, whilst the web can be pulled between the gap for being treated. In this execution, the sonotrode may be rotatably mounted.

In an alternative execution, the flexible elongated member may be mounted to a cylindrical anvil frame such as in the form of a rotatable anvil roll, as generally known in the art. Such an anvil roll may have a diameter significantly larger than the key cross-sectional dimension of the flexible elongated member, often more than 5 times, or even more than 10 times thereof. In this execution, there may be a single flexible elongated member around the circumference of the anvil roll, or several ones. The flexible elongated member may be in the form of a circle perpendicular to the axis of the anvil roll or at an angle thereto. It may also have an irregular curvilinear form on the surface, which may be a closed loop. A flexible elongated member may also intersect another one, such as when one is positioned around a drum like support and another shorter struts-like member intersects such that a y-, +- or x-like crossing is created. Accordingly, a single member may comprise such crossings, or other members may be positioned without intersecting the first. Alternatively, the flexible elongated member may only be present on certain segments of the anvil roll, and missing in others. In a preferred particular execution as described in more detail herein below, the flexible elongated member can have varying predetermined shapes.

In a particular execution, the flexible elongated member is embedded in a groove such that the upper (i.e. oriented towards the sonotrode) tangent of the flexible elongated member is positioned above the surrounding surface.

In a particular execution of the present invention, when the flexible elongated member is a solid or hollow wire, it creates a single continuous consolidation region in the form of a line. This may be particularly useful for separating materials along this line. In other execution, as may be the case when chains or tubular members with circumferential ribs are employed, these may create columns of consolidation regions, which may be considered as a series of points on a curve. Such a curve may represent a bonding curve, which may be a straight line, either in x-direction or at an angle thereto, though for many applications a curved line is preferred, i.e. the curve length of the flexible elongated member may be longer than the shortest distance between the its endpoints on the support surface.

Preferably, the x-y-directional curvature of a bonding line is shaped by a shaping device, i.e. a means for holding the flexible elongated member in a predetermined position. Preferably, the predetermined shape of the bonding curve can be readily changed without changing hardware parts, possibly even without interrupting the web movement respectively stopping the machine.

In a particular execution, the fixation of endpoints of the flexible elongated member on the anvil frame suffices to define the curve, especially if this is a straight line, but also when simple geometric curves are desired. In this embodiment, the web should be held in the appropriate positioning by a web guide means such as vacuum or high friction surfaces.

In a further particular execution, the shaping device is a groove or slot in the anvil frame, into which the flexible elongated member is embedded. The upper (y-) tangent of the flexible elongated member may extend above the web support surface so as to allow appropriate contact of the web to the thermal energy supply unit.

In case that y- or z-directional dimensions of the flexible elongated member change over its length, the groove width (y-direction) and/or depth (z-direction) may change accordingly such that the distance between the second anvil, which may comprise the energy source, and the y-tangent of the anvil remains essentially constant over the length of the flexible elongated member. Alternatively, the positioning of the second anvil may be adjusted, such as by a constant force or pressure control unit.

Yet a further and often preferred execution comprises one or more fixation means to affix the flexible elongated member in a desired position and prevent undesired lateral (y-directional) movement during the consolidation step. To this end, the anvil frame may comprise y-directionally moveable pins or plungers, for dislocating the flexible elongated member y-directionally by means of rails, air cylinders, moveable rollers, hydraulic actuators, servo motors, magnetic or other appropriate actuators.

A further particular execution of the present invention provides an improved contact and/or an increased contact time between the web and the second anvil. When the support structure of the first anvil is in the form of a cylindrical roll, its surface will pass the second anvil at the tangent to the cylinder in the gap, and consequently also the web will only have direct contact and compression along a line, particularly if the second anvil has a flat surface oriented towards the gap. Thus, if the flexible elongated member exhibits a sufficiently high longitudinal flexibility, such as may be readily accomplished when using the above describe helical anvil members, this allows lifting it such as by guide bars or guiding rollers just before and/or after the gap (along the process direction) from the cylinder surface towards the second anvil. This allows an increased processing time for the consolidation step and enables to hold the material in a convex, concave, or linear position while being consolidated.

In a second aspect, the present invention is a method for creating one or more consolidation region(s) in one or more web(s). The method includes the following steps:
  a) Providing a web comprising thermoplastic, i.e. meltable or plastically deformable material, the web exhibiting an x- or machine direction, a y- or cross-machine direction, and a z- or thickness direction. As described in the above, such a web may be a single web, or a composite web, and may comprise fibres and/or films.
  b) Forming a gap corresponding to the z-direction of the web between a first anvil comprising a flexible elongated member supported by a first anvil support structure, and a second anvil. The flexible elongated anvil element exhibits in the gap region a z-directional flexibility which is higher than the corresponding one of the anvil element support structure.
  c) Feeding the web to the gap.
  d) Setting the z-directional gap width or the gap pressure between the second anvil and flexible elongated anvil element to a pre-determined level. This level is determined according to the properties of the web as well as to the desired properties of the resulting web.
  e) Optionally providing energy to induce a temperature increase in the web or in predetermined regions thereof. Whilst the following step of compressing may be sufficient to heat the material, it may be often desired to have some of the heating separately from the compression.
  f) Compressing the web in a predetermined pattern in the gap, thusly creating the one or more consolidation region(s).

A particular benefit of this approach becomes apparent when the one or more webs exhibit fluctuations around a pre-determined target of at least one of their web properties, in particular basis weight, density, thickness, or composition. For the process step d), the predetermined level of the gap width or gap pressure corresponds to a pre-determined target of such a web property. Because of the particular flexibility and shape of the flexible elongated member, such fluctuation can be buffered away quite readily, resulting in much more uniform consolidation regions and hence also more uniform web properties.

In a third aspect, the present invention is a web comprising one or more consolidation region(s) of particular shape and which may be arranged in a particular pattern.

In the consolidation regions, the thermoplastic meltable material is molten or at least sufficiently softened so as to allow plastic deformation. The consolidation region exhibits a certain geometric extension, both with regard to the x-y-dimensions of the web, as can be seen in a x-y-top view of the web and to the z-directional dimension, as can for example be seen in a cross-sectional view of the thickness of the web. It is a particular feature of the present invention that the consolidation regions in the webs have generally an indented surface like a trough being deeper (z-directionally) in the centre than towards the margins. Such an indentation may have in an x-y-view the shape of a rectangle, a trapeze, or an ellipsis, or a frusto-ellipsoidal shape, but preferably not a circular one. The indentations having a cylindrical, ellipsoidal or frusto-ellipsoidal shape exhibit varying depth. The first and the second may be visualized by considering a cylinder respectively an ellipsoid creating an impression, the third by visualizing an ellipsoid, of which a cap or sector is cut away is creating an impression. That will create an essentially flat surface in the region, where the cup is cut away, and a curved one outwardly thereof. A skilled person will readily realize that the size and depth of the consolidation region will depend on the material properties as well as on the process settings.

The transition from a consolidation region to the surrounding regions is significantly smoother at least in one direction than for conventional consolidation regions, which open out via a steeper angle into the region outwardly thereof, thusly forming cross sections exhibiting a sharp transition, which deteriorates mechanical properties and softness of the material. In contrast, the consolidation regions as produced according to the present invention provide a particular balance of tactile properties and strength, in particular the elliptic consolidation regions. The longer axis of the ellipse or of the cylinder may be aligned with any major direction of the web, though in a particular embodiment the major axis may be at an angle of more than 1° and less than 45° to the cross-machine direction of the web. Such an angled positioning of a consolidation region provides a further degree of freedom in the adjustment of properties of the web, in particular of balancing machine-directional versus cross-machine directional strength.

Typically, though not necessarily, several consolidation regions form one or several readily recognizable intermittently repeating pattern(s). Therein a row of regions is a group of regions that are arranged predominantly along the cross-direction whilst in a column the group of regions is arranged predominantly along the machine direction.

The pattern may be a linear pattern, wherein the centre points of adjacent consolidation regions are aligned along a straight or curvilinear line, or it can be a two-dimensional pattern, such as when two or more linear patters are arranged adjacently, often parallel, to each other. The consolidation regions may also be arranged in two or more patterns, which may intermesh or overlay.

As is usual practice, the consolidation pattern can be described by the number of consolidation regions per unit area, and or relative area coverage of the consolidation regions in percent of total unit area.

In a first embodiment, the molten material is partly removed from the consolidation region, such that effectively a predetermined weakening of the web or even a hole or an aperture can be achieved. In a second embodiment, more molten materials remains in the consolidation region, which is then often referred to as a "bond point". Such a bond point may be used for bonding or consolidating components of such a web, such as when the untreated web or batt comprises loose fibres. Also, bonding may be performed between strata or layers of one or more webs, such as when spun-laid or melt blow layers are positioned on each other, bonding can be achieved across all or some of these layers or strata. Similarly, bonding may be achieved between two or more webs, which may differ in at least one property, such as a film and a fibrous web. Further, a web according to the present invention may comprise an aperture in one of the layers but a bond point in one or preferably two enveloping webs.

Fibre or foam containing webs according to the present invention provide improved tactile softness. Without wishing to be bound by the theory, it is believed, that this improvement results from the gradual transition of a fibrous or porous structure around the consolidation regions to the molten centre of the regions.

The possibility of creating very fine bonding patterns, which can e.g., be readily produced when employing tubular members with circumferential ribs, such as coil springs, further allows to seam materials with a very soft seam, wherein the structure of the seam is sufficiently fine and neighbouring bond points are close enough together to prevent liquids to penetrate through. This is particularly useful in the application on absorbent articles, wherein liquid, such as urine or low viscosity faecal matter, may be retained by water impermeable webs. Such webs may be determined by the industry standards (Rising Column Strike Through)—AATCC 127-1985 or an equivalent method such as provided by INDA (formerly the International Nonwovens and Disposables Association, now The Association of the Nonwoven Fabrics Industry) or EDANA (European Disposables And Nonwovens Association). Preferably, a seam made according to the present invention provides a hydrohead, which is more than 80%, more preferably more than 90% of the value of that seamed material, which exhibits the lowest hydrohead performance. Preferably, a seam shows a hydrohead of at least 60 mm water, preferably of at least 100 mm.

In the following, particular executions of the present invention are described in more detail. This description, however, should not be seen in any limiting way.

FIG. 1A shows schematically an enlarged top view of a consolidation region 110 in a web 100, here shown as nonwoven web, according to the present invention, as may be produced by a helical anvil. The web comprises fibres 120 made of thermoplastic meltable material, here shown as a batt of loose, essentially endless fibres 120, such as may be the result of a spunmelting process, with interstices 123 between the fibres. The web exhibits a machine direction 102 and a cross-machine direction 104 perpendicular thereto. The consolidation region has an elliptical shape with a larger, major axis 112, and a shorter, minor axis 118. The major axis of the consolidation region is at an angle 116 relative to the cross-machine direction 104 of the web. The consolidation region comprises a centre consolidation region, indicated by the ellipse 108 and the circumscribing transition region of the consolidation region 109.

FIG. 1B shows a cross-sectional view (not to scale) along the cross-machine direction, showing the extension of the web along the z-direction 106 of the web 100 and of the elliptical consolidation region 110 with its centre region 108 and its transition region 109. The web is shown with a smoothed surface indicated by dotted line 125. In the consolidation region 110, one of the surfaces, here shown as the upper one, is indented, and the material underneath the centre region of the indentation is plastically deformed into solid material. The shape of the surface of the indentation can be described by a part of the surface of an ellipsoid, here shown with a dotted line 126. The indentation has a depth 128, and the consolidation region has its minimum thickness 127. Such an indentation may be achieved by various processes with heating and compressing, as discussed herein in more detail, but for the present explanation it should be noted, that the compression is achieved by a curved structure pressing against a flat structure, and henceforth the compression will be to the highest extent in the centre portion of the indentation. Consequently, the plasticized material of this region will be squeezed laterally outwardly into the loose fibre batt in the transition region 109 and flow around unmolten fibres. Henceforth, there will be a much smoother transition as compared to conventional embossing processes.

This smoother transition will still exist, even if the indentation has a flat section, as indicated in FIG. 1C. Therein, the indentation can be thought to be created by a frusto-ellipsoid i.e. an ellipsoid with a flattened surface, such if a cap of the ellipsoid would be truncated along a plane. Henceforth, the indentation of the consolidation region would have a flat section 126' and a curved one 126". Accordingly, the indentation has a depth 128' and the consolidation point has its minimum thickness 127'.

A skilled person will readily realize that for a given material the minimum thickness of the consolidation region 127, 127' —or the corresponding depth of the indentation 128, 128' —depend on the compression respectively the gap width of the compressing anvils. If the gap width is set to very small values, the height will approach zero and an aperture may be formed. Also, for a set gap width, the height will depend on the amount of material as determined by the local basis weight of the web in the consolidation region. Because of the combined mechanism of compressing and laterally squeezing, any variation of the basis weight in the web will be compensated to a much higher degree than hitherto, and the properties of the consolidated web will be much more uniform.

Figure 1D:
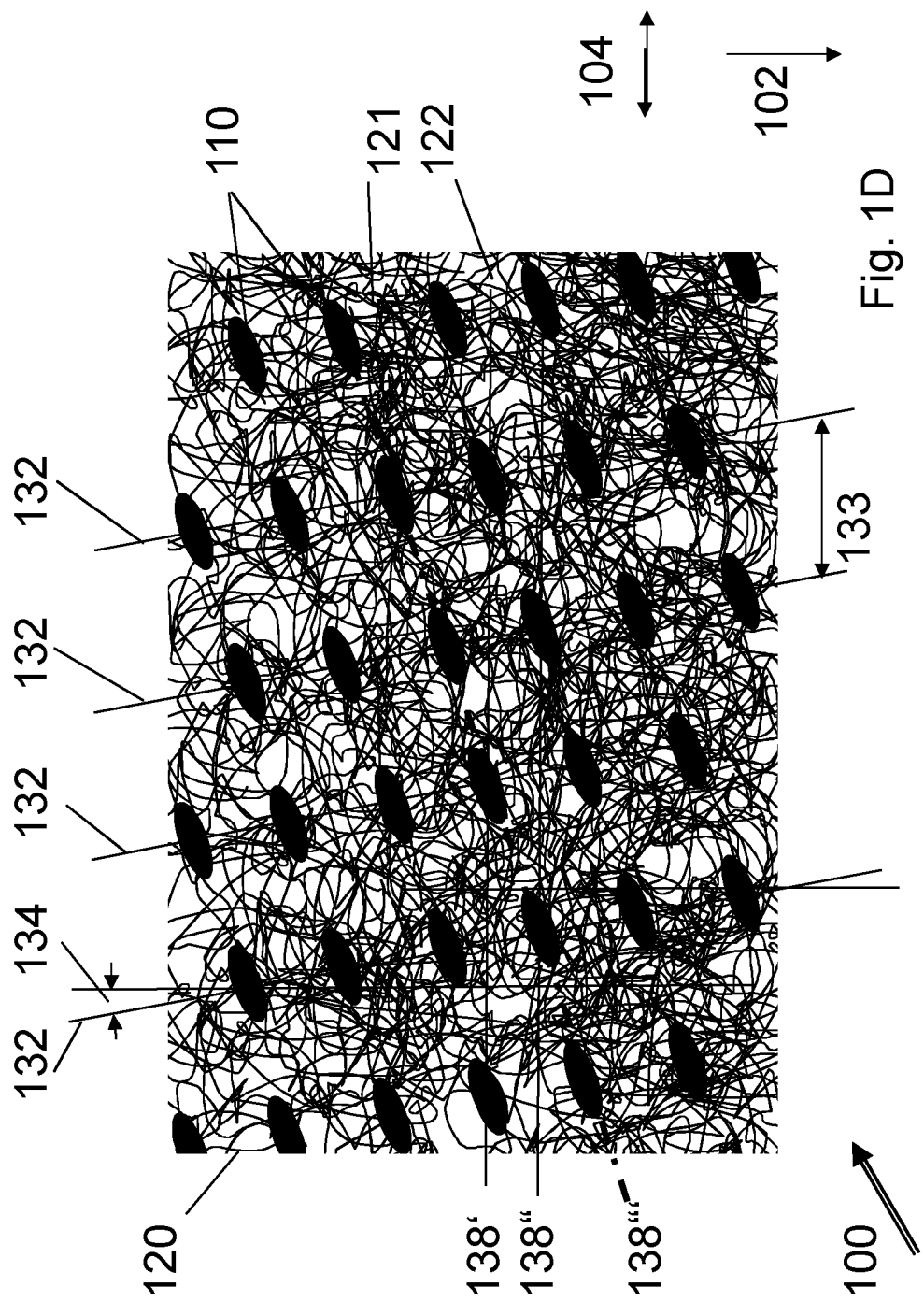

FIG. 1D shows schematically a top view of such a web 100 with regions with fewer fibres and lower basis weight 121 and regions with more fibres and higher basis weight 122. Therein, it is also shown that the consolidation regions may be arranged in a pattern. The pattern can be described by having the consolidation regions arranged in columns 132 and rows 138. The columns can be aligned with the machine direction 102 of the web, or as shown in the figure, have a column angle 134 relative to the machine direction. The neighbouring columns can have a cross-machine directional column distance 133. As shown, two neighbouring columns are machine directionally offset by half of the distance of two machine-directionally neighbouring consolidation regions, such that a staggered pattern exists.

Whilst also valid for columns, it is shown in the figure for the rows, that such a pattern can be described in several ways, namely the rows may be defined along lines 138' in combination with lines 138" (i.e. two overlaying patterns), whereby the latter is cross-directionally offset by the column distance 133, or by a row lines 138'''. As shown, the axes of the consolidation regions 120 are neither aligned with the machine direction 102 nor with the pattern lines 132 or 138.

In FIG. 2 a preferred execution for the apparatus for creating consolidation regions is described. Therein, the flexible elongated, in this particular case the tubular anvil element with circumferential ribs is executed as a spiral spring. FIG. 2A shows a top view and with CD and MD cross-sectional views in FIGS. 2B and 2C respectively. FIG. 2D depicts a cross-sectional view of a flexible elongated, in this particular case helical anvil element. In these figures, a web 1000 is moving along machine (x-) direction 102 on a web and anvil element support 1100. A heat source, such as a ultrasonically operating sonotrode 2000 is positioned to form a gap 5100 with a helical anvil element 3000 with an outer helix diameter 3010, wire diameter 3020, wire distance 3030 and helical anvil endpoints 3200 and 3300 positioned in the anvil support 1100 an anvil groove 3600. The gap width corresponds to the smallest distance between the sonotrode 2000 and the uppermost (i.e. oriented towards the sonotrode) tip of the helical anvil element. Also indicated are consolidation regions or bonding spots 4000 of the web (not all shown).

In a particular execution, a flexible elongated, in this particular case helical anvil was used in the form of a spiral extension spring (i.e. adjacent coil wires were contacting each other) having an outer/coil diameter of about 8.9 mm and being made up of a circular wire having a diameter of approximately 1.8 mm, the helix had a pitch of about 5.55 threads/cm, exhibiting 10 mm deflection in the flexibility test. The spiral was positioned in a groove of approximately 9 mm width and a depth of approximately 8 mm. The groove was made from plywood, which was sufficiently rigid and non-deformable for the present application. A manually operated ultrasonic sonotrode as available from Sonic Italy, Rho, Milan, Italy, with approximately 20 kHz frequency and a circular sonotrode head of 6 mm was hand held and guided over the spiral spring and two layers of a conventional spun-bonded nonwoven web of approximately 27 $g/m^2$, thereby generating a bonding pattern of consolidation regions having an elliptical extension of about 1 mm for the longer axis and approximately 0.6 mm for the shorter axis. The consolidation regions were spaced apart (midpoint to midpoint) at approximately 1.8 mm, corresponding to the wire diameter. Visual inspection indicated an indented surface and a smooth transitioning from the consolidation region to neighbouring unconsolidated regions. In a first execution, the spiral was positioned straight, i.e. the axis of the spiral was a straight line. The longer axis of the consolidation regions exhibited an angle of approximately 10° to this axis. In a second execution, the groove with the spiral therein was curvilinearly bent, similar to the execution shown in FIG. 2. The longer axis of the ellipsoidal consolidation regions exhibited a similar angle as above to the tangent to the axis of the spiral.

In a further execution, the same settings were used to bond two layers of conventional PE film, such as used as a backsheet material for disposable articles, exhibiting a basis weight of 18 $g/m^2$, instead of the nonwoven webs. Also in this execution, the consolidation resulted in a well defined and sufficiently strong seam.

In yet a further particular execution, a spiral having an outer coil diameter of 6.5 mm with a circular wire of approximately 1.2 mm wire diameter and 8.3 threads/cm, exhibiting a deflection of more than 50 mm in the flexibility test was employed under otherwise same conditions, the consolidation regions had a longer axis of approximately 0.75 mm and a shorter axis of approximately 0.4 mm. Visual inspection indicated an indented surface and a smooth transitioning from the consolidation region to neighbouring unconsolidated regions.

In an even further particular execution, a spiral having an outer coil diameter of 7.0 mm with a circular wire of approximately 0.6 mm wire diameter and about 17 threads/cm, exhibiting a deflection of more than 50 mm in the flexibility test was employed under otherwise same conditions, the consolidation regions had a longer axis of approximately 1.0 mm and a shorter axis of approximately 0.3 mm. Visual inspection indicated an indented surface and a smooth transitioning from the consolidation region to neighbouring unconsolidated regions. Further tests were performed with an iron litz having an outer diameter of about 1.2 mm, made of litz wires each with a diameter of about 0.1 mm and twisted to about 13 wires/cm, exhibiting a deflection of about 49 mm in the flexibility test. A bendable and flexible iron wire of 3.5 mm diameter exhibited a deflection of 0.3 mm in the flexibility test, and a solid PVC plastic wire having a diameter of about 3 mm exhibited about 39 mm deflection in the flexibility test. All executions exhibited good seam strength.

In a comparative example, a chain of magnetically connected metal spheres each having a diameter of approximately 3 mm was placed in the groove as described in the above and two webs were analogously treated. The bonding resulted in essentially circular consolidation regions having a diameter of approximately 0.3 mm, spaced apart at 3 mm, corresponding to the diameter of the spheres. Thus the bonding of this embodiment does not exhibit any directional preferences. Further, in this execution, the maximum consolidation percentage is lower than for the executions with the helical spring, and seam strength, although maybe sufficient for certain applications, was about 30% of that achieved with the coils, i.e. significantly lower.

FIG. 7 depicts a particular execution of a set up as described in the context of FIG. 2 hereinabove. In this execution, the energy source is an ultrasonic horn, or a sonotrode, and a damper element 3700 is positioned between the flexible elongated, in this particular case tubular anvil element and the support structure. In an exemplary execution, the damper element is a conventional hard rubber strip having a thickness of about 4 mm. In a further exemplary execution, the damper element is a commercially available foam material, e.g. available as "3M 03809 sanding sponge fine" having a thickness of about 5 mm. For both examples, the bonding was at least as good as with the other examples made with a tubular anvil supported by a more rigid or less elastic support structure.

In FIG. 3, further exemplary options for tubular anvils with circumferential ribs are shown. FIG. 3A depicts a top view of a flexible elongated, in this particular case helical anvil element in the form of a spiral spring 3000 as discussed in the context of FIG. 2 with a helix axis 3015 and a helix/thread angle 3018. Also indicated are ellipses 3100, which depict the portion of the wire, that may penetrate into the web and form a consolidation region 100 as discussed in the context of FIG. 1 with major and minor axes as well as angles as described therein. As the wire distance between two neighbouring wires is essentially zero, the distance of the centre points of two neighbouring ellipses corresponds to the wire diameter 3020.

It should be noted, that upon bending of the helical anvil element the helix axis will also bend. Henceforth, the angles as described herein will be local angles. Also, the wire distance may change from the left to the right side (when considering the orientation as in FIG. 3A). FIG. 3B depicts an embodiment as in FIG. 3A, except that the cross-section of the wire is not circular, but the wire shape has flattened circles, such as when two symmetric segments along a chord are cut off a wire having the wire diameter 3020. The wire distance will now be smaller than the wire diameter, whilst a consolidation region in a web may still have the same size, but two neighbouring consolidation regions will be closer together.

Yet a further option for a helical anvil element is depicted in FIG. 3C with a cross-sectional view through a hexagonically shaped wire and FIG. 3D, where secondary wire 3050 is shown to be wound around a hexagonal core. The execution of FIG. 3D may result in a particular consolidation region as shown in FIG. 3E, wherein the primary consolidation region 110 corresponding to the contact ellipse of the tubular anvil 3100 shown in an enlarged view is made up of secondary or sub-regions 111.

FIG. 3F depicts an even further execution for a flexible elongated, in this particular case tubular anvil element with circumferential ribs as may be formed from shim rings mounted on a core 3065. To this end, larger shim rings 3060 may alternate with smaller shim rings 3062. The core may be made of a flexible material, onto which the shim rings are mounted while it is in an extended state, such that it may contract after mounting and further stabilize the shims.

Also an execution for a tubular anvil with circumferential ribs as shown in FIG. 3G is contemplated to be within the scope of the present invention, where a conventional corrugated or convolute tubing or pipe is used, e.g. with a circular cross-section, as shown in FIG. 3H or a rectangular one with rounded corners as shown in FIG. 3I.

FIG. 4A shows a preferred embodiment wherein the bonding curve, e.g. the y-dimensional dislocation of the tubular anvil away from its straight configuration, is determined by the deformation of the helical anvil by laterally moveable fixation means 5000.

As shown, the curve length 3500 of the helical anvil is longer than the shortest distance 3400 between the helical anvil endpoints 3200 and 3300 on the anvil support, which may be cylindrical roll.

Figure 4B:
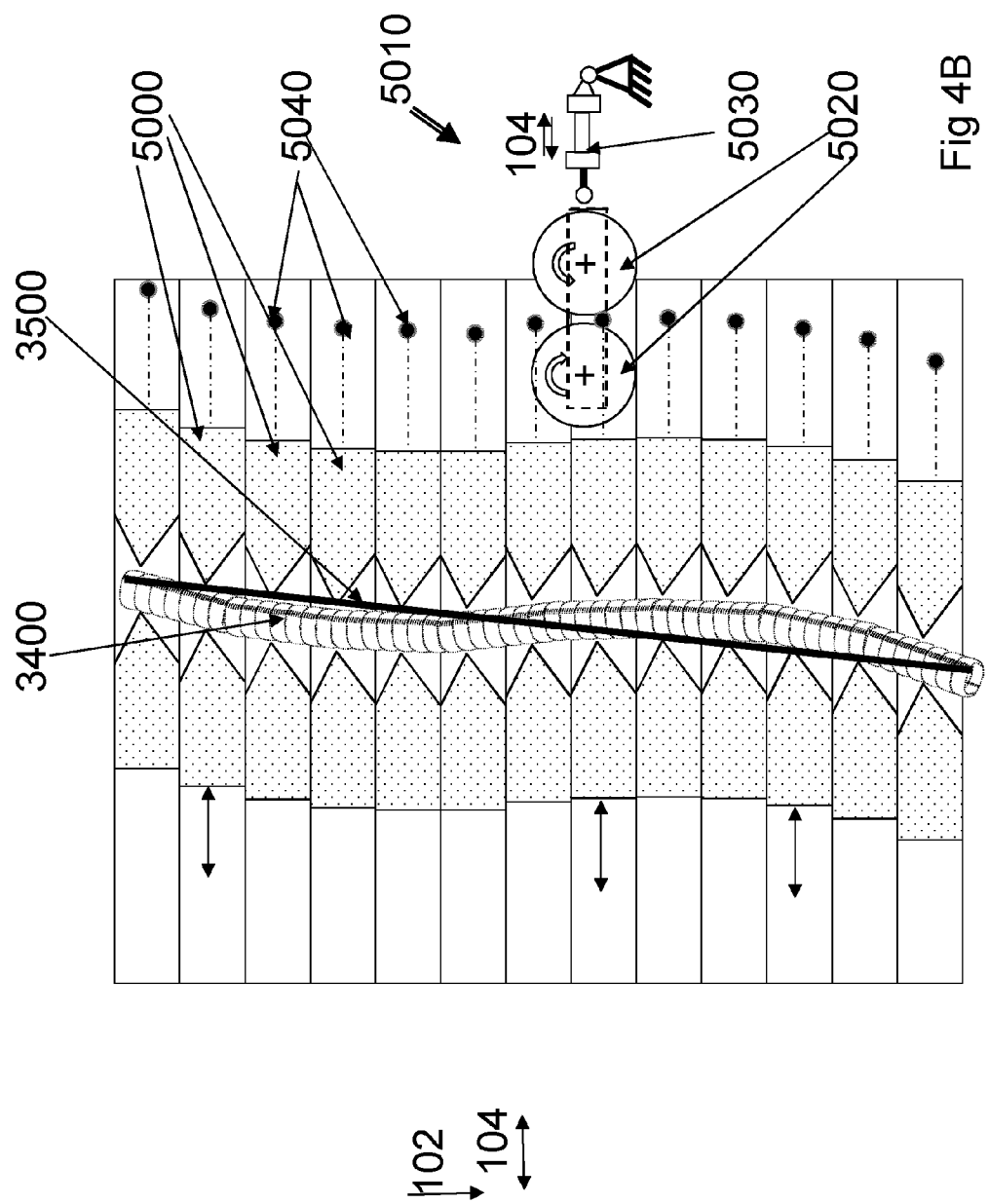
FIGS. 4A and B show schematically a particular execution for shaping a flexible tubular anvil element according to the present invention.

As shown in FIG. 4B the fixation means 5000 are in a different lateral position, thereby creating a differently shaped bonding curve. The helical anvil can accommodate varying curve lengths as the endpoint 3200 and 3300 can move slightly in the x-direction, when a different curve shape is set. Alternatively, the end points may be fixed, and the helical anvil is slightly extended by increasing wire distance 3030 as curves are formed which differ from a straight line.

Also shown in FIG. 4B is an exemplary curvature shaping means 5010, here shown as two guide wheels 5020, which are translatorily moveable such as by a linear drive 5030 connected to a fixed frame in the gap region. The wheels 5020 interact with guide pins 5040, which are connected to the moveable fixations means 5000. Upon movement along the machine direction 102 of the pins 5040 and the cross-directional (104) movement of the guide wheels 5020, the shape of the bonding curve can be adjusted continuously.

Figure 6A:
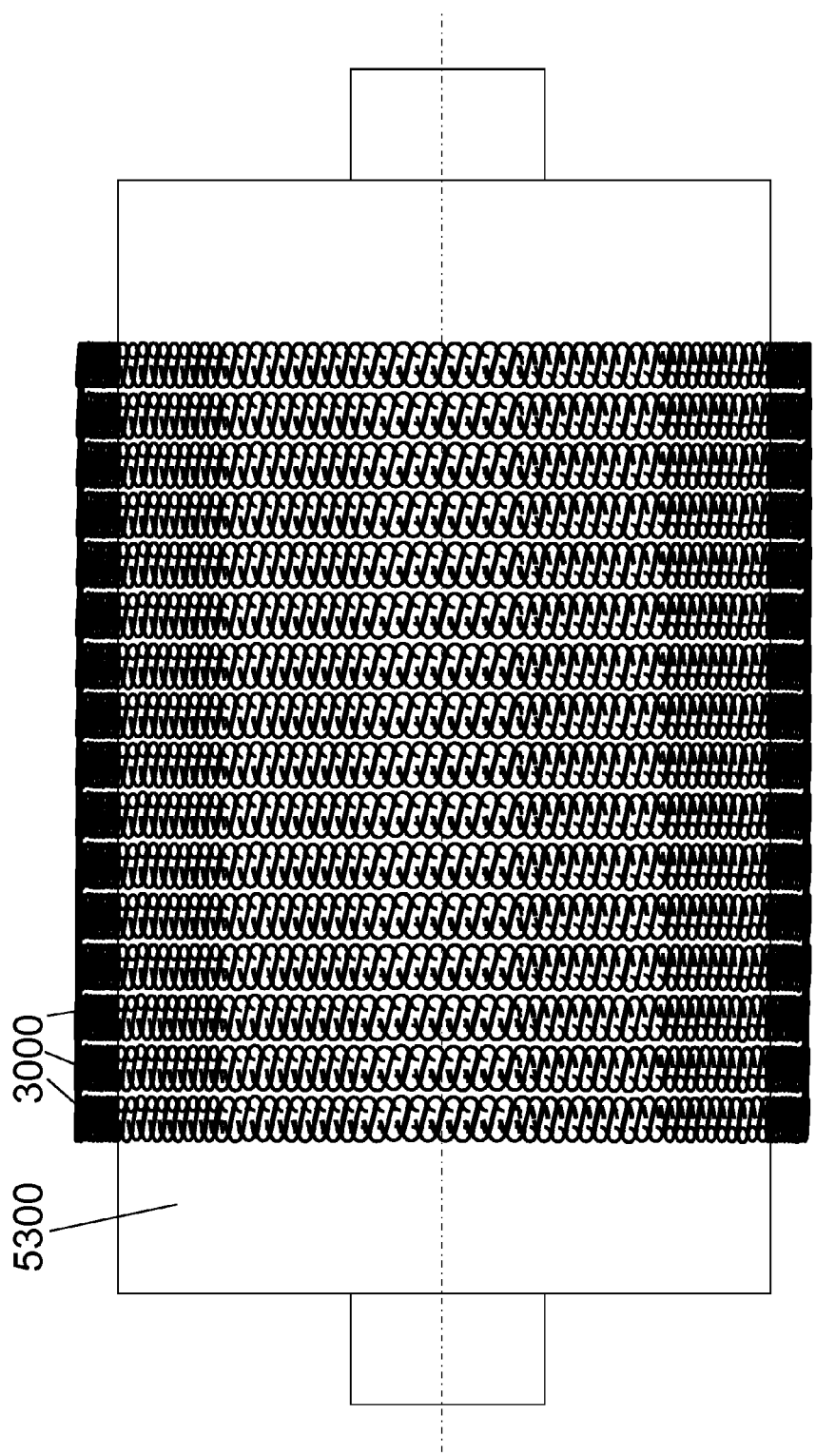
FIGS. 6A and B show schematically an equipment set up for consolidating webs.

FIG. 5A shows schematically how a flexible elongated, in this particular case tubular anvil element may be positioned on the surface of an anvil support, such as an anvil roll 5300. The tubular anvil element 3000, counteracts with an energy source, such as a sonotrode, 2000 and the web (not shown) is consolidated in the gap 5100. A further design is depicted in FIG. 5B. Therein is shown an additional anvil element guide means 5200, which is affixed stationary relative to the energy source. The flexible anvil element, such as a spiral spring, is guided over the guide means such that it is lifted from the surface of the anvil support. As a result, the flexible anvil element is passing underneath the energy source e.g. along a straight line rather than a circular one for an embodiment as shown in FIG. 5A. Henceforth the process time for interacting with the energy source in prolonged and the interaction may now be over the full surface of the energy source rather than only along a contact line. In this setup, the material also is forced into another shape than that of the anvil roll at the material infeed. FIG. 6A describes further executions which may be particularly beneficial if not only a column of consolidation points is desired but a full array. To this end, several flexible elongated, in this particular case tubular anvil elements 3000 may be positioned next to each other on the surface of an anvil support 5300. Each may be a closed spiral, or a single spiral may be wound around the support.

Yet a further variant is depicted in FIG. 6B. Similar to the execution shown in FIG. 6A, several anvil elements, here in the form of a spiral spring, are positioned adjacently. However, the wire distance is extended, such as by stretching the spiral spring, such that the wires of a neighbouring spiral or spiral portion may be inter-digitizingly positioned into such a wire gap, as indicated by arrows 6000. This allows a broad flexibility for designing various consolidation region patterns with varying numbers of consolidation regions per unit area and consolidation region area percentage.

A further execution for a flexible elongated element is depicted in FIG. 8A showing a chain 7000 of hollow cylindrically shaped elements 7010 exhibiting a comparably low elasticity in themselves, which are connected to each other at pivoting joints 7040, here shown by a continuous chain core element 7030 running through the hollow centre of the cylinders. The chain core element may be a flexible band or string, and may also be elastic. The overall flexibility of the chain can now be adjusted by the tightness of cylinders fitting on the string, by the extension of the string, if elastic, and by the distance between adjacent cylindrical elements. FIG. 8B depicts schematically a corresponding cylindrical indentation forming a consolidation point.

The invention claimed is:

1. An apparatus
for consolidating one or more region(s) of one or more web(s), which comprise(s) thermoplastic material and which exhibit a length (x-), width (y-) and thickness (z-) direction, by plastic deformation,
said apparatus exhibiting a x- or machine direction aligned with the direction of movement of said web(s) relative to said apparatus, a y- or cross-machine direction aligned with the width direction of the web(s),
said apparatus comprising:
one or more energy source(s) for increasing the temperature at least of said region(s) of said web(s);
a first and a second anvil forming a gap and adapted to receive said web(s) there between such that the thickness or z-direction of said webs is aligned with the gap width; and
a gap width adjustment means adapted to apply pressure to said web(s) in said gap,
wherein said first anvil comprises
a flexible elongated member which is flexible at least in its y- and z-direction, and
a first anvil support structure.

2. The apparatus according to claim 1, wherein said flexible elongated member forming the first anvil has a x-directional extension which is at least twice as long as the average of its main cross-sectional dimensions in the x-z plane.

3. The apparatus according to claim 1, wherein said flexible elongated member of said first anvil exhibits a degree of flexibility enabling more than 0.1 mm of deflection.

4. The apparatus according to claim 1, wherein said flexible elongated member comprises metal.

5. The apparatus according to claim 1, wherein said first anvil support structure exhibits a hardness higher than the hardness of said elongated member.

6. The apparatus according to claim 1, wherein said first anvil support structure is a planar support or a cylindrical roll.

7. The apparatus according to claim 1, wherein said first anvil support structure is a cylindrical roll, said apparatus further comprising an anvil element lifting device positioned stationary relative to the gap and adapted to lift up portions of said flexible elongated member from said support structure in or adjacently to the gap region.

8. The apparatus according to claim 1, further comprising a damper element positioned between said elongated anvil member and said anvil support and exhibiting a flexibility which is higher than the one of said flexible elongated element and of said flexible element support structure.

9. The apparatus according to claim 1, wherein said flexible elongated member has an outer dimension in y- and z direction of less than 20mm.

10. The apparatus according to claim 1, wherein at least a portion of said flexible elongated anvil element is positioned on or recessed in the surface of said support structure.

11. The apparatus according to claim 1, further comprising an flexible elongated member shaping means adapted for y-directionally displacing predetermined portions of said flexible elongated anvil elements.

12. The apparatus according to claim 1, wherein at least one of said energy sources emits sonic, preferably ultrasonic energy.

13. The apparatus according to claim 1, wherein said elongated member of said first anvil is selected from the group of
i) wires,
ii) chains being a series of connected elements, wherein the elements exhibit a flexibility which is lower than the one of the total chain and which are pivotally or inter-meshingly or inter-engagingly connected to form the chain, and
iii) tubular members with circumferential ribs.

14. The apparatus according to claim 13, wherein said wires have a spherical or an elliptic cross-section, or have a hollow core.

15. The apparatus according to claim 13, wherein said chains comprise cylindrical or frusto-conical elements lined up on a flexible core.

16. The apparatus according to claim 13, wherein said tubular members with circumferential ribs are selected from the group consisting of a helical spring, litz wires, shim rings mounted on a flexible core, and bellowed, corrugated, finned flexible tubes.

17. The apparatus according to claim 16, wherein said tubular anvil element is a helical spring comprising a coil wire having a cross-sectional shape which is circular, elliptical, flattened spherical, or hexagonal.

18. The apparatus according to claim 17, wherein said coil wire has a maximum outer diameter of less than 10 mm.

* * * * *